(12) United States Patent
Sakai et al.

(10) Patent No.: US 6,228,820 B1
(45) Date of Patent: *May 8, 2001

(54) METHOD FOR USING THERMALLY STABLE ESTERS IN A LUBRICATING OIL FOR A REFRIGERATING MACHINE

(75) Inventors: Akimitsu Sakai; Toshiya Hagihara, both of Wakayama (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/863,049

(22) Filed: May 23, 1997

Related U.S. Application Data

(63) Continuation-in-part of application No. PCT/JP96/02738, filed on Sep. 20, 1996.

(30) Foreign Application Priority Data

Sep. 25, 1995 (JP) ................................. 7-272040
Dec. 28, 1995 (JP) ................................. 7-354489

(51) Int. Cl.[7] ............................ C10M 105/38; C09K 5/04
(52) U.S. Cl. ............................................. 508/485; 252/68
(58) Field of Search .................................. 508/485, 486, 508/489; 252/68

(56) References Cited

U.S. PATENT DOCUMENTS

| | | |
|---|---|---|
| 3,115,519 | 12/1963 | Crouse et al. . |
| 3,282,971 | 11/1966 | Metro et al. . |
| 4,826,633 * | 5/1989 | Carr ..................................... 508/485 |
| 5,202,044 | 4/1993 | Hagihara et al. . |
| 5,395,544 | 3/1995 | Hagihara et al. . |
| 5,470,497 * | 11/1995 | Schlosberg ............................. 252/68 |
| 5,486,302 | 1/1996 | Short . |

FOREIGN PATENT DOCUMENTS

| | | |
|---|---|---|
| 0536940 | 4/1963 | (EP) . |
| 0435253 | 7/1991 | (EP) . |
| 6-17073 * | 1/1994 | (JP) . |
| 6108076A | 4/1994 | (JP) . |
| 6-108076 * | 4/1994 | (JP) . |
| 6-184575 * | 7/1994 | (JP) . |
| 9409096 | 4/1994 | (WO) . |

* cited by examiner

*Primary Examiner*—Margaret Medley
(74) *Attorney, Agent, or Firm*—Birch, Stewart, Kolasch and Birch, LLP

(57) ABSTRACT

An ester compound having thermal stability in the presence of a metal characterized in that the ester compound is formed between a dihydric to nonahydric hindered alcohol having 5–15 carbon atoms and a saturated aliphatic monocarboxylic acid having 3–20 carbon atoms or a derivative thereof; that the ratio of a branched carboxylic acid or a derivative thereof to the entire carboxylic acids or derivatives thereof is not less than 50 mol %; that the hydroxyl value of the ester compound is not more than 30 mg KOH/g; and that the acid value after a sealed tube test is not more than 10 mg KOH/g; and a lubricating oil composition comprising the ester compound in an amount of not less than 50% by weight. The present invention provides an ester compound having outstandingly good thermal stability in the presence of a metal and a lubricating oil composition and a working fluid composition for a refrigerating machine comprising the ester compound as the main component.

6 Claims, 6 Drawing Sheets

AV: Acid value

METHOD FOR USING THERMALLY STABLE ESTERS IN A LUBRICATING OIL FOR A REFRIGERATING MACHINE

This application is a continuation-in-part of PCT international application No. PCT/JP96/02738 which has an international filing date of Sep. 20, 1996, which designated the United States, the entire contents of which are hereby incorporated by reference.

TECHNICAL FIELD

The present invention relates to an ester compound, a lubricating oil composition and a working fluid composition for a refrigerating machine. More specifically, the present invention relates to an ester compound which has excellent thermal stability in the presence of a metal, and to a lubricating oil composition and a working fluid composition for a refrigerating machine which contain as the main component the ester compound.

BACKGROUND ART

As industrial machinery increases in power and decreases size with the advance of industrial technology, the conditions under which a lubricating oil is used have become increasingly severe. Furthermore, in order to reduce the burden on the environment, the policy of saving energy and environmental resources is also applicable to lubricating oils. With such social trends, even better performance, such as improved thermal stability, excellent oxidation stability, higher viscosity index, lower volatility and better fluidity at low temperatures, have been required of lubricating oils, and mineral oil-based lubricating oils have gradually been replaced with synthetic lubricating oils. It is noted that esters, in particular hindered esters, are used for engine base oils, grease base oils, working fluids, turbine oils, heat carrier oils, metal working oils and refrigerating oils.

Since the above-mentioned various lubricating oils are used for the purposes or under conditions which keep them almost always in contact with a metal, various requirements for oil performance should always be met in the presence of a metal.

Esters, however, are subject to thermal decomposition in the presence of a metal at high temperatures, causing a problem of generating carboxylic acids or metal carboxylates. In particular, the above problem occurs with a lubricating oil used for compressors for refrigeration machines, such as refrigerators, where a hindered ester is used as a refrigerating oil for a substitute refrigerant.

Also, the use of chlorodifluoromethane (HCFC22), which is now used for room air conditioners, packaged air conditioners and refrigeration machines for industrial use, has recently been decided to be restricted or banned in the near future, and a hydrofluorocarbon mixture has been proposed as a candidate for an alternative. The use of such hydrofluorocarbon mixture increases the pressure inside a compressor when compared with the use of 1,1,1,2-tetrafluoroethane (HFC134a) which is currently used for refrigerators. In particular, when it is used for a rotary compressor or a scroll compressor, the refrigerating oil used therefor is exposed to severe thermal conditions. Thus, the concern about the above problem is further increased.

In order to avoid these problems, the use of lubricating oils which are thermally stable in the presence of a metal, such as alkylated diphenylethers and perfluoropolyethers, has been considered. However, these compounds are generally expensive and when alkylated diphenylether is used as a refrigerating oil, its insolubility in hydrofluorocarbon refrigerants becomes a problem.

For the above reasons, a lubricating oil which is thermally stable in the presence of a metal and less expensive has been in demand.

Incidentally, the fact that a metal (iron) exerts an influence on the thermal stability of an ester compound is described in R. L. COTTINGTON et al. [ASLE Trans. 12, 280–286 (1969)] and SATISH K. NAIDU et al. [Wear, 121(1988) 211–222].

It has been pointed out that the addition of TCP (tricresylphosphate) to the base oil is effective to improve thermal stability in the presence of a metal (Report by the above mentioned R. L. COTTINGTON et al.). However, there is no teaching at all about the relation between the thermal stability in the presence of a metal and the structure of ester compounds. That is, neither the feasibility for improving the thermal stability of an ester compound used as a base oil nor the guideline for the selection of ester structures, if such improvement has been possible, is taught.

On the other hand, it has been reported in various publications that ester compounds having a particular structure, that is, those formed from branched carboxylic acids, have an excellent performance as a lubricating oil.

Specifically, for obtaining ester compounds having excellent oxidation stability, use of fatty acids having 2 side chains at the $\alpha$- or $\beta$- position to the carbonyl group, as the starting material for hindered esters, is disclosed in the specifications of U.S. Pat. No. 3,115,519, U.S. Pat. No. 3,282,971, British Patent No. 999099, and British Patent No. 1028402. Also, Japanese Patent Laid-Open No. 55-105644 and some other publications disclose that hindered esters prepared from 3,5,5-trimethylhexanoic acid and a linear carboxylic acid at a ratio of 90:10 to 10:90 is excellent in oxidation stability. Also, Japanese Patent Laid-Open No. 5-17787 and some other publications disclose that hindered esters prepared from 5–90% neopentyl branched fatty acids and 95–10% linear fatty acids and/or α-branched fatty acids are excellent in heat resistance. However, no discussion is made as to the heat resistance in the presence of a metal.

Moreover, in Japanese Patent Laid-Open No. 6-158079, a carboxylic acid ester having a branch at the 2- or 3-position is described as a lubricating oil composition having excellent oxidation stability and a good viscosity index, but the publication also mentions that a carboxylate having a branched structure and a linear carboxylate are comparable to each other and have no difference in oxidation stability.

As mentioned above, there have been no reports which discuss the thermal stability of an ester compound in the presence of a metal.

In the field of refrigerating oils, esters to be used in conjunction with hydrofluorocarbons containing HFC 32 are disclosed in Japanese Patent Laid-Open Nos. 5-17789, 5-32985, 5-239480, 6-17073, and 8-502769, and the ratio of branched acyl groups to the entire acyl groups is specified in some of the above publications. However, all these publications only mention the compatibility with hydrofluorocarbons containing HFC 32.

Also, esters for which the ratio of branched acyl groups to the entire acyl groups is specified are disclosed in Japanese Patent Laid-Open Nos. 3-200895, 4-311797, 4-314793, and 5-209171. However, these publications only mention the compatibility with HFC134a and the hydrolysis resistance.

In Japanese Patent Laid-Open Nos. 3-217493 and 5-25484, esters for which hydroxyl value is specified are disclosed. These publications only mention wear resistance and elution of PET oligomer.

Moreover, Japanese Patent Laid-Open No. 6-108076 discloses esters for which the ratio of branched acyl groups to the entire acyl groups and hydroxyl value are specified. However, it only mentions hydrolysis resistance in the presence of HFC134a.

As described above, there are no reports on the thermal stability of esters in the presence of hydrofluorocarbons containing HFC32.

DISCLOSURE OF THE INVENTION

A first object of the present invention is to provide a hindered ester compound which has good thermal stability in the presence of a metal. Also, a second object of the present invention is to provide a lubricating oil composition and a working fluid composition for a refrigerating machine comprising as the main component the ester compound. A third object of the present invention is to provide a method for increasing the thermal stability of a lubricating oil which comes into contact with a metal by blending the ester compound with the lubricating oil.

The present inventors made intensive studies to achieve the above objects. As a result, they found that a hindered ester compound obtained from a hindered alcohol and a particular branched carboxylic acid has significantly improved thermal stability even in the presence of a metal, and have thus completed the present invention.

In brief, the present invention is directed to:

(1) An ester compound having thermal stability in the presence of a metal formed from a dihydric to nonahydric hindered alcohol having 5 to 15 carbon atoms, or mixtures thereof; and a saturated aliphatic monocarboxylic acid having 3 to 20 carbon atoms or a derivative thereof or mixtures thereof; wherein the ratio of a branched carboxylic acid or a derivative thereof to the entire carboxylic acids or derivatives thereof is not less than 50 mol %; wherein the hydroxyl value of the ester compound is not more than 30 mg KOH/g and the acid value of the ester compound is not more than 10 mg KOH/g, the acid value being measured after carrying out the steps comprising (a) adjusting the water concentration of 5 g of the ester compound to not more than 10 ppm, (b) placing the ester compound, along with iron, copper and aluminum pieces each having a diameter of 1.6 mm and a length of 100 mm, in a glass vessel with an inner volume of about 15 ml, (c) degassing the vessel to a pressure of not more than 1.3 Pa, (d) placing I g of a difluoromethane/pentafluoroethane/1,1,1,2-tetrafluoroethane mixture at a weight ratio of 23:25:52, (e) sealing the vessel, and (f) maintaining the vessel at 250° C. for 3 days;

(2) A lubricating oil composition comprising the ester compound of item (1) above in an amount of not less than 50% by weight;

(3) A working fluid composition for a refrigerating machine comprising a lubricating oil composition of item (2) above and hydrofluorocarbons;

(4) A method for increasing thermal stability of a lubricating oil, wherein the method comprises using the ester compound of item (1) above, as a base oil of the lubricating oil which comes into contact with a metal;

(5) A method for preventing thermal degradation of a lubricating oil, wherein the method comprises using the ester compound of item (1) above, as a base oil of the lubricating oil which comes into contact with a metal;

(6) Use of the ester compound of item (1) above, comprising using the ester compound, as a base oil of a lubricating oil in a rotary compressor for a refrigerating machine or a scroll compressor for a refrigerating machine, thereby maintaining thermal stability of the lubricating oil which comes into contact with a metal; and (7) Use of the ester compound of item (1) above, comprising using the ester compound, as a base oil of a lubricating oil in a compressor for room air conditioners or a compressor for packaged air conditioners, thereby maintaining thermal stability of the lubricating oil which comes into contact with a metal.

BRIEF DESCRIPTION OF THE DRAWINGS

In FIG. 1, numeral 1 denotes a compressor, 2, 3, and 5–7 denote pipes, 4 denotes a capillary tube, 8 denotes an accumulator, 9 denotes a cooling fan, 10 denotes valves, 11 denotes a heat exchanger, and HP and LP respectively denote a pressure gauge.

DETAILED DESCRIPTION OF CARRYING OUT THE INVENTION

Figure 1:
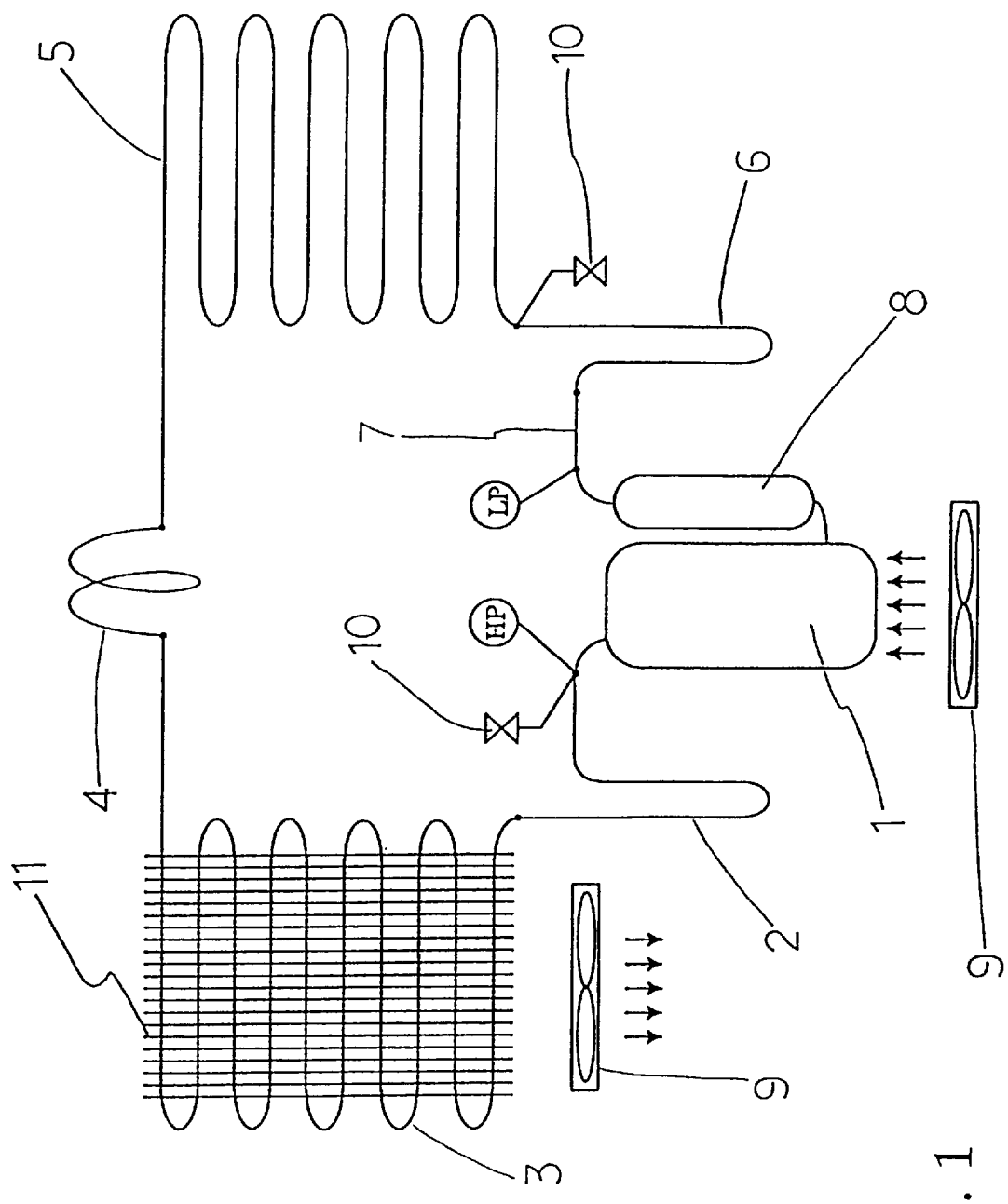
FIG. 1 is a diagram of an apparatus used for a compressor test.

The ester compound of the present invention is thermally stable in the presence of a metal. It is formed by reacting a dihydric to nonahydric hindered alcohol having 5 to 15 carbon atoms with a saturated aliphatic monocarboxylic acid having 3 to 20 carbon atoms or a derivative thereof. The ratio of a branched carboxylic acid or a derivative thereof to the entire carboxylic acids or derivatives thereof is not less than 50 mol %; that the hydroxyl value of the ester compound is not more than 30 mg KOH/g; and that the acid value of the ester compound is not more than 10 mg KOH/g, wherein the acid value is measured after adjusting the water content of 5 g of the ester compound to not more than 10 ppm, placing the ester compound, along with iron, copper and aluminum pieces each having a diameter of 1.6 mm and a length of 100 mm, in a glass vessel having an inner volume of about 15 ml, degassing the inside of the vessel to not more than 1.3 Pa, charging the vessel with 1 g mixture of difluoromethane/pentafluoroethane/1,1,1,2-tetrafluoroethane=23:25:52 (weight ratio), sealing the vessel, and keeping the vessel at 250° C. for 3 days.

The term "hindered alcohol" used in the present invention is an alcohol which has no hydrogen atoms on the carbon at the β-position of a hydroxyl group. It has better thermal stability as compared with a conventional alcohol which has a hydrogen atom at the β-position. Also, the number of carbon atoms of the hindered alcohol is 5 to 15, and the number of hydroxyl groups is 2 to 9. The number of hydroxyl groups is two or more from the viewpoint of imparting appropriate viscosity to the ester compound, and 9 or less from the viewpoint of avoiding unnecessarily high viscosity. The number of hydroxyl groups is preferably 2 to 6, more preferably 2 to 4. The structure having no ether bonds in the molecule is preferred from the viewpoint of imparting thermal stability to the alcohol backbone.

Examples of the above hindered alcohols include neopentyl glycol, 2-ethyl-2-methyl-1,3-propanediol, 2-isopropyl-2-methyl-1,3-propanediol, 2,2-diethyl-1,3-propanediol, 2-ethyl-2-n-butyl-1,3-propanediol, trimethylolethane, trimethylolpropane, pentaerythritol, and dipentaerythritol.

Among the above examples, preference is given to neopentyl glycol, trimethylolpropane and pentaerythritol because these are readily available for industrial use and inexpensive.

The above hindered alcohols may be used singly or in combination of two or more kinds according to necessity.

The number of carbon atoms of the saturated aliphatic monocarboxylic acid (carboxylic acid moiety in case of a carboxylic acid derivative) used in the present invention is 3 to 20, preferably 4 to 18, more preferably 5 to 12. The number of carbon atoms of the carboxylic acid is 3 or more, preferably 4 or more, more preferably 5 or more, still more preferably 7 or more from the viewpoint of suppressing corrosiveness to metals and imparting viscosity suitable for lubricating oils, and it is 20 or less, preferably 18 or less, more preferably 12 or less from the viewpoint of avoiding unnecessarily high viscosity. In particular, when the ester compound obtained is used for a working fluid composition for a refrigerating machine, the number of carbon atoms is preferably 4 to 12, more preferably 4 to 9, still more preferably 5 to 9, particularly preferably 7 to 9. From the viewpoint of the solubility in hydrofluorocarbons, it is preferably 12 or less, more preferably 9 or less.

In the carboxylic acid or a derivative thereof used in the present invention, the ratio of a branched carboxylic acid or a derivative thereof to the entire carboxylic acids or derivatives thereof (hereinafter simply referred to as branched ratio) is 50 mol % or more, preferably 60 molt or more, more preferably 70 mol % or more, still more preferably 80 mol % or more, still more preferably 90 mol % or more, still more preferably 95 mol % or more, particularly preferably 98 mol % or more, very preferably 99 mol % or more.

The branched ratio less than 50 mol % is undesirable because it tends to become difficult to obtain expected thermal stability of ester compounds in the presence of a metal.

Examples of the saturated aliphatic branched monocarboxylic acids having 3 to 20 carbon atoms used in the present invention include isobutyric acid, pivalic acid, 2-methylbutyric acid, 2-methylvaleric acid, 3-methylvaleric acid, 4-methylvaleric acid, 2,2-dimethylbutyric acid, 2-ethylbutyric acid, tert-butylacetic acid, 2,2-dimethylpentanoic acid, 2,4-dimethylpentanoic acid, 2-ethylpentanoic acid, 3-ethylpentanoic acid, 2-methylhexanoic acid, 3-methylhexanoic acid, 5-methylhexanoic acid, 2-ethylhexanoic acid, 3-ethylhexanoic acid, 3,5-dimethylhexanoic acid, 2,4-dimethylhexanoic acid, 3,4-dimethylhexanoic acid, 4,5-dimethylhexanoic acid, 2,2-dimethylhexanoic acid, 2-methylheptanoic acid, 3-methylheptanoic acid, 6-methylheptanoic acid, 2-propylpentanoic acid, 2,2-dimethylheptanoic acid, 3,5,5-trimethylhexanoic acid, 2-methyloctanoic acid, 2-ethylheptanoic acid, 3-methyloctanoic acid, 2-ethyl-2,3,3-trimethylbutyric acid, 2-isopropyl-2,3-dimethylbutyric acid, 2,2,4,4-tetramethylpentanoic acid, 2,2,3,3-tetramethylpentanoic acid, 2,2,3,4-tetramethylpentanoic acid, 2,2-diisopropylpropionic acid, 2,2-dimethyloctanoic acid, 3,7-dimethyloctanoic acid, 2-butyloctanoic acid, isotridecanoic acid, 2-(3'-methylbutyl)-7-methyloctanoic acid, 2-(1'-methylbutyl)-5-methyloctanoic acid, 2-hexylnonanoic acid, 2-methyltetradecanoic acid, 2-ethyltridecanoic acid, 2-methylpentadecanoic acid, 2-hexyldecanoic acid, 2-heptyldecanoic acid, 2-(1',3',3'-trimethylbutyl)-4,6,6-trimethylheptanoic acid, 2-(3'-methylhexyl)-6-methylnonanoic acid, 2-heptylundecanoic acid, 2-(1',3',3'-trimethylbutyl)-5,7,7-trimethyloctanoic acid, 2-(3'-methylhexyl)-7-methyldecanoic acid, isostearic acid, isononadecanoic acid and isoeicosanoic acid.

Among the carboxylic acids presented above, those having 4 to 12 carbon atoms are suitably used as a saturated aliphatic monocarboxylic acid, when the ester compound of the present invention is used for a working fluid composition for a refrigerating machine. Particular preference is given to 2-methylbutyric acid, 3-methylbutyric acid, 2-ethylbutyric acid, 2-methylhexanoic acid, 2-ethylpentanoic acid, 2-ethylhexanoic acid and 3,5,5-trimethylhexanoic acid from the viewpoint of availability.

In the present invention, in order to improve the thermal stability in the presence of a metal of the ester compound of the present invention, contact of carbonyl groups with a metal surface is blocked. Thus, it is desired for the ester compound to have a large number of branched chains in the structure and branched chains at the α-position of the carbonyl group. In this respect, neo acids having a quaternary carbon atom at the α- or β-position of the carbonyl group are particularly preferred, but from the viewpoint of fluidity of the ester compound at low temperatures, branched carboxylic acids other than neo acids are preferred. From the above viewpoints, 2-methylhexanoic acid, 2-ethylpentanoic acid, 2-ethylhexanoic acid, and 3,5,5-trimethylhexanoic acid are preferred; 2-ethylhexanoic acid and 3,5,5-trimethylhexanoic acid are more preferred, with particular preference being given to 2-ethylhexanoic acid.

The number of carbon atoms of an aliphatic linear carboxylic acid (the moiety of carboxylic acid in case of a carboxylic acid derivative) which may be blended with an aliphatic branched monocarboxylic acid used in the present invention is 3 to 20, preferably 4 to 18, more preferably 5 to 12. The number of carbon atoms of the carboxylic acid is 3 or more, preferably 4 or more and more preferably 5 or more from the viewpoint of suppressing corrosiveness to metals and imparting viscosity suitable for lubricating oils, and the number of carbon atoms is 20 or less, preferably 18 or less and more preferably 12 or less from the viewpoint of avoiding unnecessarily high viscosity and imparting fluidity at low temperatures. In particular, when the ester compound is used for a working fluid composition for a refrigerating machine, the number of carbon atoms is preferably 4 to 12, more preferably 4 to 8, and particularly preferably 5 to 8; and from the viewpoint of solubility in hydrofluorocarbons, it is 12 or less, particularly preferably 8 or less.

Examples of the mixable saturated aliphatic linear monocarboxylic acid having 3 to 20 carbon atoms include propionic acid, butyric acid, valeric acid, caproic acid, enanthic acid, caprylic acid, pelargonic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, and eicosanoic acid.

Among the above examples, those having 4 to 12 carbon atoms are used as a mixable saturated aliphatic linear monocarboxylic acid, when the ester compound of the present invention is used for a working fluid composition for a refrigerating machine. Among the above carboxylic acids, particular preference is given to valeric acid, caproic acid, enanthic acid, and caprylic acid.

As derivatives of the above aliphatic monocarboxylic acids, esters of lower alkyls having 1 to 3 carbon atoms, such as methyl ester and ethyl ester as well as acid anhydrides, are included. The term "carboxylic acid moiety" in case of such derivatives of aliphatic monocarboxylic acids means a moiety of an acyl group of the derivatives.

The above carboxylic acids or derivatives thereof may be used singly or in combination of two or more kinds.

The ester compound used in the present invention can be formed between the above-mentioned hindered alcohol and monocarboxylic acid or a derivative thereof by conventional esterification or transesterification.

When two or more alcohols or two or more carboxylic acids are used to obtain the ester compound used in the present invention, the alcohols or carboxylic acids may be mixed prior to the reaction, or ester compounds, each prepared by the reaction between one alcohol and one carboxylic acid, may be blended to obtain a desired composition.

When the ester compound of the present invention is used for a lubricating oil composition, the kinematic viscosity at 40° C. is normally 2 to 1000 mm$^2$/s from the viewpoint of easiness in handling, energy saving, wear resistance, and lubricity. It is preferably 2 to 500 mm$^2$/s, more preferably 2 to 200 mm$^2$/s, still more preferably 5 to 200 mm$^2$/s, still more preferably 8 to 200 mm$^2$/s, still more preferably 15 to 200 mm$^2$/s, still more preferably 15 to 100 mm$^2$/s, still more preferably 20 to 90 mm and particularly preferably 20 to 75 mm$^2$/s. When the lubricating oil composition containing an ester compound of the present invention is used for rotary compressors, scroll compressors, compressors for room air conditioners and compressors for packaged air conditioners, the kinematic viscosity at 40° C. of the ester compound of the present invention is preferably 40 to 90 mm$^2$/s, more preferably 50 to 75 mm$^2$/s, particularly preferably 55 to 75 mm$^2$/s, and most preferably 60 to 75 mm$^2$/s from the viewpoint of energy saving and wear resistance.

It is desired that the melting point or the pour point of the ester compound of the present invention is as low as possible from the viewpoint of low operation temperatures of machines and facilitating the starting of machines. It is normally 0° C. or less, preferably −10° C. or less, more preferably −20° C. or less.

Ester compounds having such preferable kinematic viscosity, low pour point and low melting point include ester compounds formed between two or more carboxylic acids and one or more hindered alcohols. Among them, ester compounds formed between two or more carboxylic acids selected from the group consisting of 2-methylhexanoic acid, 2-ethylpentanoic acid, 2-ethylhexanoic acid, 3,5,5-trimethylhexanoic acid and derivatives thereof and one or more hindered alcohols are preferred.

Specifically, the carboxylate mixtures mentioned below are exemplified. The carboxylate mixtures are particularly preferred when the ester compound, as a lubricating oil composition for a refrigerating machine, is used for a working fluid composition for a refrigerating machine.

It is preferable that the acid value of the ester compound of the present invention is as low as possible from the viewpoint of corrosiveness to metals and thermal stability of the ester compound in the presence of metals. It is normally 0.5 mg KOH/g or less, more preferably 0.1 mg KOH/g or less, more preferably 0.05 mg KOH/g or less, still more preferably 0.03 mg KOH/g or less, particularly preferably 0.01 mg KOH/g or less.

From the viewpoint of wear resistance, hygroscopicity, thermal stability in the presence of a metal and ease of in production, hydroxyl value of the ester compound of the present invention is preferably 0.01 to 30 mg KOH/g. The lower limit of the above hydroxyl value is more preferably 0.1 mg KOH/g. The upper limit of the above hydroxyl value is more preferably 20 mg KOH/g, more preferably 15 mg KOH/g, still more preferably 10 mg KOH/g, still more preferably 8 mg KOH/g, particularly preferably 5 mg KOH/g. Specifically, the range of hydroxyl value is more preferably 0.01 to 20 mg KOH/g, more preferably 0.01 to 15 mg KOH/g, more preferably 0.01 to 10 mg KOH/g, more preferably 0.01 to 8 mg KOH/g, more preferably 0.01 to 5 mg KOH/g. Moreover, the range is still more preferably 0.1 to 20 mg KOH/g, still more preferably 0.1 to 15 mg KOH/g, still more preferably 0.1 to 10 mg KOH/g, still more preferably 0.1 to 8 mg KOH/g, particularly preferably 0.1 to 5 mg KOH/g.

The ester compound of the present invention has an acid value of 10 mg KOH/g or less, where the acid value is measured after adjusting the water content of 5 g of the ester compound to not more than 10 ppm, placing the ester compound, along with iron, copper and aluminum piece each having a diameter of 1.6 mm and a length of 100 mm, in a glass vessel with an inner volume of about 15 ml, degassing the inside of the vessel to not more than 1.3 Pa, charging the vessel with 1 g mixture of difluoromethane/ pentafluoroethane/1,1,1,2-tetrafluoroethane=23:25:52 (weight ratio), sealing the vessel, and keeping the vessel at 250° C. for 3 days. Here, the acid value as mentioned above is preferably 5 mg KOH/g or less, more preferably 2 mg KOH/g or less. In the present specification, the above procedures are referred to as a sealed tube test, which is conducted to evaluate thermal stability of an ester compound in the presence of a metal under static conditions.

The expression "thermal stability in the presence of a metal" used for the present invention means resistance to thermal decomposition observed when an ester compound is made to coexist with a metal for a certain period of time at a high temperature under the conditions where the influence of oxygen is eliminated. The lower the degree of thermal decomposition, the better the thermal stability.

Specifically, thermal stability is evaluated by measuring acid value of the test oil after a test comprising placing 10 g of a test oil (an ester compound) which has been sufficiently degassed and adjusted to have a water content of 10 ppm or less in advance and an iron piece having a diameter of 1.6 mm and a length of 150 mm in a glass vessel with an inner volume of about 30 ml, sufficiently degassing the inside of the vessel to 1.3 Pa or less, sealing the vessel, and keeping the vessel at 250° C. for 3 days. In this test, from the viewpoint of better thermal stability in the presence of a metal, the acid value measured after the test is preferably 10 mg KOH/g or less, more preferably 5 mg KOH/g or less, particularly preferably 3 mg KOH/g or less, most preferably 1 mg KOH/g or less.

The effects of the present invention cannot be evaluated by the method specified in JIS K-2540, which is a testing method for thermal stability of lubricating oil because the evaluation is carried out in the absence of a metal. The evaluation methods specified in JIS K-2276 and JIS K-2242 cannot be used because the evaluation is carried out under conditions for evaluating oxidation stability.

It is desired that the ester compound of the present invention has an acid value of not more than 1.0 mg KOH/g, when it is measured after a compressor operation comprising charging a 1 kW rotary compressor (G515QB1X manufactured by Hitachi, Ltd.) with 450 g of the ester compound of which water content has been adjusted to not more than 20 ppm in advance and a given amount of a mixture of difluoromethane/pentafluoroethane/1,1,1,2-tetrafluoroethane=23:25:52 (weight ratio) to achieve a compressor shell top temperature of 130° C., a discharge pressure of 26 kgf/cm$^2$ and an inlet pressure of 5 kgf/cm$^2$ and continuously running the compressor for 400 hours. The above mentioned acid value is more preferably 0.8 mg KOH/g or less, most preferably 0.7 mg KOH/g. In the present specification, the above test is referred to as a compressor test, which evaluates thermal stability of ester compounds in the presence of hydrofluorocarbons and a metal under dynamic conditions. The amount of the above mixture used in the compressor test is not particularly limited as long as the temperature and pressure conditions as mentioned above are satisfied.

Here, the apparatus used for the compressor test is detailed with reference to FIG. 1.

FIG. 1 is a diagram of an apparatus used for a compressor test. Numeral 1 is a compressor, which is a 1 kW rotary compressor (G515QB1X manufactured by Hitachi, Ltd.). A copper pipe 2 is connected to the discharging side of the compressor 1, the pipe 2 having an outer diameter of 6.35 mm, an inner diameter of 4.72 mm, and a length of 700 mm.

The pipe 2 is further connected to another copper pipe 3 at its end, the pipe 3 having an outer diameter of 9.52 mm, an inner diameter of 7.92 mm, and a length of 6000 mm. An aluminum heat exchanger 11 is fixed onto the pipe 3. Numeral 8 is an accumulator which is originally attached to the compressor 1. To the accumulator 8, a copper pipe 7 having an outer diameter of 9.52 mm, an inner diameter of 7.92 mm, and a length of 100 mm is connected. At the end of the pipe 7, another copper pipe 6 having an outer diameter of 6.35 mm, an inner diameter of 4.72 mm and a length of 700 mm is connected. At the end of the pipe 6, another copper pipe 5 having an outer diameter of 9.52 mm, an inner diameter of 7.92 mm, and a length of 4000 mm is connected. A copper capillary tube 4 having an inner diameter of 2 mm and a length of 400 mm connects the pipe 3 to the pipe 5. Numeral 9 is a cooling fan for controlling the conditions of the compressor test, which operates in connection with the temperature of the compressor. Numeral 10 is a valve for sealing an ester compound as a test oil, and flon. HP and LP respectively indicate a pressure gauge.

When a compressor test is carried out using the apparatus of FIG. 1, a desired temperature and pressure are achieved by adjusting the amount of the mixture of difluoromethane/ pentafluoroethane/1,1,1,2-tetrafluoroethane=23:25:52 (weight ratio) within the range of 160 to 180 g.

In the ester compound of the present invention, the branched ratio of the carboxylic acid moiety is not less than 50 mol %, and the hydroxyl value of the ester compound is not more than 30 mg KOH/g. The following are examples of ester compounds having a preferred combination of branched ratio and hydroxyl value.

1) An ester compound having a branched ratio of the carboxylic acid moiety of not less than 70 mol % and a hydroxyl value of not more than 20 mg KOH/g, more preferably not more than 15 mg KOH/g, particularly preferably not more than 5 mg KOH/g.

2) An ester compound having a branched ratio of the carboxylic acid moiety of not less than 50 mol % and a hydroxyl value of not more than 10 mg KOH/g, more preferably not more than 5 mg KOH/g.

3) An ester compound having a branched ratio of the carboxylic acid moiety of not less than 90 mol % and a hydroxyl value of not more than 30 mg KOH/g, more preferably not more than 25 mg KOH/g, particularly preferably not more than 15 mg KOH/g.

4) An ester compound having a branched ratio of the carboxylic acid moiety of not less than 80 mol % and a hydroxyl value of not more than 15 mg KOH/g, more preferably not more than 10 mg KOH/g, particularly preferably not more than 5 mg KOH/g.

Here, the ester compound of the above combination 1) has a desired property with respect to thermal stability under static conditions evaluated by a sealed tube test, and the ester compounds of the above combinations 2) and 3) have a desired property with respect to thermal stability under both static and dynamic conditions which are evaluated by a sealed tube test and a compressor test, respectively. The ester compound of the above combination 4) has high thermal stability in the absence of oxygen and hydrofluorocarbons.

The ester compound of the present invention is usable as a base oil for a lubricating oil composition, and a lubricating oil composition containing the ester compound of the present invention as the main component can be used in combination with hydrofluorocarbons as a working fluid composition for a refrigerating machine.

Also, the lubricating oil composition of the present invention having excellent thermal stability in the presence of a metal can suitably be used as engine oils, grease, hydraulic oils, turbine oils, heat transfer oils, metal working oils, refrigerating oils, etc., among which it is particularly suitable for refrigerating oils.

Among refrigerating oils, it is particularly suitably used as a refrigerating oil for rotary compressors or scroll compressors because the temperature and pressure inside such compressors become so high that thermal stability of refrigerating oils in the presence of a metal is highly required.

Also, among refrigerating oils, the lubricating oil composition of the present invention which has excellent thermal stability in the presence of a metal is particularly suitable for use in combination with hydrofluorocarbons containing difluoromethane (HFC32), especially hydrofluorocarbons containing difluoromethane and pentafluoroethane (HFC125) or hydrofluorocarbons containing difluoromethane, pentafluoroethane and 1,1,1,2-tetrafluoroethane (HFC134a), because the inside of a compressor is exposed to a higher temperature and a higher pressure as compared with the case where only 1,1,1,2-tetrafluoroethane is used.

The lubricating oil composition of the present invention is suitably used as lubricating oils for hermetic compressors of refrigerators, refrigerating machines for industrial use, room air conditioners and packaged air conditioners, where thermal stability in the presence of a metal is required. Among them, it is suitably used as lubricating oils for hermetic compressors of room air conditioners and packaged air conditioners where good thermal stability in the presence of a metal is particularly needed.

When the ester compound of the present invention is used as a base oil for a lubricating oil composition, the ester compound of the present invention contained in the lubricating oil composition is preferably not less than 50% by weight, more preferably not less than 80% by weight, particularly preferably not less than 90% by weight from the viewpoint of thermal stability in the presence of a metal. Other lubricating oils blended therewith are not particularly limited, and it is desired to use lubricating oils which do not impair the thermal stability of the lubricating oil composition in the presence of a metal.

In particular, when the lubricating oil composition containing the ester compound of the present invention is used for a working fluid composition for a refrigerating machine, the ratio of the ester compound of the present invention in the lubricating oil composition is preferably 80% by weight or more, more preferably 90% by weight or more, particularly preferably 95% by weight or more, most preferably 98% by weight or more. In particular, when it is used for rotary compressors, scroll compressors, or compressors for room air conditioners and packaged air conditioners, or when it is used along with hydrofluorocarbons containing difluoromethane (HFC32), the amount of the ester compound of the present invention is preferably 90% by weight or more, more preferably 95% by weight or more, particularly preferably 98% by weight or more, most preferably 99% by weight or more.

The kinematic viscosity at 40° C. of the lubricating oil composition of the present invention is preferably 2 to 500 mm$^2$/s, more preferably 2 to 200 mm$^2$/s, still more preferably 5 to 200 mm$^2$/s, still more preferably 8 to 200 mm$^2$/s, still more preferably 15 to 200 mm$^2$/s, still more preferably 15 to 100 mm$^2$/s, still more preferably 20 to 90 mm$^2$/s, particularly preferably 20 to 75 mm$^2$/s.

In particular, when the lubricating oil composition of the present invention is used for rotary compressors and scroll compressors for refrigerating machines, compressors for room air conditioners and compressors for packaged air conditioners, kinematic viscosity at 40° C. of the lubricating oil composition of the present invention is preferably 40 to 90 mm$^2$/s, more preferably 50 to 75 mm$^2$/s, particularly preferably 55 to 75 mm$^2$/s, most preferably 60 to 75 mm$^2$/s from the viewpoint of energy saving and wear resistance.

It is desired that the melting point or the pour point of the lubricating oil composition of the present invention is as low as possible and it is usually not higher than 0° C., preferably not higher than −10° C., more preferably not higher than −20° C.

In the lubricating oil composition of the present invention, various known additives for lubricating oils may be used in an amount so as not to impair thermal stability. Such additives include antioxidants, extreme pressure agents, oiliness improvers, defoaming agents, detergent dispersants, anticorrosive agents, demulsifiers, viscosity index improvers, metal deactivators, and pour point depressants.

The working fluid composition for a refrigerating machine of the present invention contains the above-mentioned lubricating oil composition of the present invention and hydrofluorocarbons.

The working fluid composition for a refrigerating machine of the present invention is suitably used as a working fluid composition for a refrigerating machine for rotary compressors and scroll compressors because of its excellent thermal stability in the presence of a metal. Since the working fluid composition for a refrigerating machine of the present invention has excellent thermal stability in the presence of a metal, it is particularly suitable as a working fluid composition for a refrigerating machine for compressors of room air conditioners and packaged air conditioners. Moreover, since the working fluid composition for a refrigerating machine of the present invention has excellent thermal stability in the presence of a metal, it is particularly effective when used in combination with hydrofluorocarbons containing difluoromethane (HFC32), particularly those containing difluoromethane and pentafluoroethane or those containing difluoromethane, pentafluoroethane and 1,1,1,2-tetrafluoroethane.

Also, since the working fluid composition for refrigeration machine of the present invention has excellent thermal stability when it comes into contact with a metal, even when used for a rotary compressor or scroll compressor of refrigerating machines, the thermal decomposition of the ester compound in the working fluid composition can be inhibited, thereby making it possible to inhibit an increase in an acid value owing to the thermal decomposition of the ester compound. Particularly in a rotary compressor or scroll compressor where higher temperature conditions are required, since the carboxylic acids are likely to be formed by thermal decomposition, metal salts thereof are produced and then cause capillary tube sealing of a refrigeration cycle. However, the composition of the present invention can solve such problems.

Therefore, the life of the working fluid composition for refrigeration machine can be made notably longer even in cases where the rotary compressor or scroll compressor is used.

When the ester compound or the lubricating oil composition of the present invention is used for a working fluid composition for a refrigerating machine, the temperature of two-phase separation with hydrofluorocarbons is desirably low, and it is not higher than 10° C., preferably not higher than 0° C., more preferably not higher than −10° C., particularly preferably not higher than −30° C., most preferably not higher than −50° C.

It is desired that the working fluid composition for a refrigerating machine of the present invention have good thermal stability in the following evaluation. Namely, 5 g of a test oil, which has been sufficiently degassed and adjusted to have a water content of not more than 10 ppm, is placed in a glass vessel with an inner volume of about 15 ml along with iron, copper and aluminum pieces each having a diameter of 1.6 mm and a length of 100 mm. After the inside of the vessel is sufficiently degassed to not higher than 1.3 Pa, it is charged with 1 g mixture of difluoromethane/pentafluoroethane/1,1,1,2-tetrafluoroethane=23:25:52 (weight ratio), sealed and allowed to stand at 250° C. for 3 days. Then, the sealed vessel is opened to remove the mixture, and acid value of the ester compound or lubricating oil composition is measured. In this test, acid value after the test is preferably not higher than 10 mg KOH/g, more preferably not higher than 5 mg KOH/g, particularly preferably not higher than 2 mg KOH/g.

When the ester compound of the present invention is used as a lubricating oil composition for a refrigerating machine in a working fluid composition for a refrigerating machine, it is desired that the ester compound has a branched ratio of not lower than 50 mol % and a hydroxyl value of not higher than 30 mg KOH/g. Moreover, examples of preferred combinations of branched ratio and hydroxyl value include the following combinations 1) to 3):

1) An ester compound having a branched ratio of the carboxylic acid moiety of not less than 70 mol % and a hydroxyl value of not more than 20 mg KOH/g, more preferably not more than 13 mg KOH/g, particularly preferably not more than 5 mg KOH/g.

2) An ester compound having a branched ratio of the carboxylic acid moiety of not less than 50 mol % and a hydroxyl value of not more than 10 mg KOH/g, more preferably not more than 5 mg KOH/g.

3) An ester compound having a branched ratio of the carboxylic acid moiety of not less than 90 mol % and a hydroxyl value of not more than 30 mg KOH/g, more preferably not more than 25 mg KOH/g, particularly preferably not more than 15 mg KOH/g.

Examples of preferred ester compounds used for the working fluid composition for a refrigerating machine include a carboxylate mixture formed between pentaerythritol and n-pentanoic acid/2-methylbutyric acid/3,5,5-trimethylhexanoic acid, a carboxylate mixture formed between pentaerythritol and n-pentanoic acid/3,5,5-trimethylhexanoic acid, a carboxylate mixture formed between neopentyl glycol and 2-ethylpentanoic acid/2-methylhexanoic acid/2-ethylhexanoic acid, a carboxylate mixture formed between trimethylolpropane and 2-ethylpentanoic acid/2-methylhexanoic acid/2-ethylhexanoic acid, a carboxylate mixture formed between pentaerythritol and 2-ethylpentanoic acid/2-methylhexanoic acid/2-ethylhexanoic acid, neopentyl glycol di-2-ethyl hexanate, trimethylolpropane tri-2-ethyl hexanate, pentaerythritol tetra-2-ethyl hexanate, neopentyl glycol di-3,5,5-trimethyl hexanate, trimethylolpropane tri-3,5,5-trimethyl hexanate, pentaerythritol tetra-3,5,5-trimethyl hexanate, a carboxylate mixture formed between neopentyl glycol and 2-ethylpentanoic acid/2-methylhexanoic acid/2-ethylhexanoic acid/3,5,5-trimethylhexanoic acid, a carboxylate mixture formed between trimethylolpropane and 2-ethylpentanoic acid/2-methylhexanoic acid/3,5,5-trimethylhexanoic acid, a carboxylate mixture formed between pentaerythritol and 2-ethylpentanoic acid/2-methylhexanoic acid/3,5,5-trimethylhexanoic acid, a carboxylate mixture formed between neopentyl glycol and 2-ethylhexanoic acid/3,5,5-trimethylhexanoic acid, a carboxylate mixture formed between trimethylolpropane and 2-ethylhexanoic acid/3,5,5-trimethylhexanoic acid, a carboxylate mixture formed between pentaerythritol and 2-ethylhexanoic acid/3,5,5-trimethylhexanoic acid, a carboxylate mixture formed between pentaerythritol and n-heptanoic acid/3,5,5-trimethylhexanoic acid, a carboxylate mixture formed between pentaerythritol and n-octanoic acid/3,5,5-trimethylhexanoic acid, a carboxylate mixture formed between pentaerythritol and n-octanoic acid/2-ethylhexanoic acid/3,5,5-trimethylhexanoic acid, a carboxylate mixture formed between trimethylolpropane and 2-ethylpentanoic acid/2-methylhexanoic acid/2-ethylhexanoic acid/3,5,5-trimethylhexanoic acid, and a carboxylate mixture formed between pentaerythritol and 2-ethylpentanoic acid/2-methylhexanoic acid/2-ethylhexanoic acid/3,5,5-trimethylhexanoic acid.

Among the above, from the viewpoint of thermal stability in the presence of a metal, particular preference is given to neopentyl glycol di-2-ethyl hexanate, trimethylolpropane tri-2-ethyl hexanate, pentaerythritol tetra-2-ethyl hexanate, a carboxylate mixture formed between trimethylolpropane and 2-ethylhexanoic acid/3,5,5-trimethylhexanoic acid, a carboxylate mixture formed between pentaerythritol and 2-ethylhexanoic acid/3,5,5-trimethylhexanoic acid, a carboxylate mixture formed between trimethylolpropane and 2-ethylpentanoic acid/2-methylhexanoic acid/2-ethylhexanoic acid, a carboxylate mixture formed between pentaerythritol and 2-ethylpentanoic acid/2-methylhexanoic acid/2-ethylhexanoic acid, a carboxylate mixture formed between trimethylolpropane and 2-ethylpentanoic acid/2-methylhexanoic acid/2-ethylhexanoic acid/3,5,5-trimethylhexanoic acid and a carboxylate mixture formed between pentaerythritol and.2-ethylpentanoic acid/2-methylhexanoic acid/2-ethylhexanoic acid/3,5,5-trimethylhexanoic acid.

From the viewpoint of energy saving and wear resistance as mentioned above, the ester compound used for the working fluid composition for a refrigerating machine of the present invention has a kinematic viscosity at 40° C. of preferably 40 to 90 mm$^2$/s, more preferably 50 to 75 mm$^2$/s.

Specific examples of such ester compounds include a carboxylate mixture formed between pentaerythritol and n-pentanoic acid/3,5,5-trimethylhexanoic acid, a carboxylate mixture formed between pentaerythritol and n-pentanoic acid/2-methylbutyric acid/3,5,5-trimethylhexanoic acid, a carboxylate mixture formed between pentaerythritol and n-heptanoic acid/3,5,5-trimethylhexanoic acid, a carboxylate mixture formed between pentaerythritol and n-octanoic acid/3,5,5-trimethylhexanoic acid, a carboxylate mixture formed between pentaerythritol and n-octanoic acid/2-ethylhexanoic acid/3,5,5-trimethylhexanoic acid, trimethylolpropane tri-3,5,5-trimethyl hexanate, a carboxylate mixture formed between pentaerythritol and 2-ethylhexanoic acid/3,5,5-trimethylhexanoic acid, and a carboxylate mixture formed between pentaerythritol and 2-ethylpentanoic acid/2-methylhexanoic acid/2-ethylhexanoic acid/3,5,5-trimethylhexanoic acid. Among them, an ester formed between a carboxylic acid mixture containing 3,5,5-trimethylhexanoic acid and pentaerythritol is more preferred because an ester with a desired viscosity can be prepared. From the viewpoint of thermal stability in the presence of a metal, particular preference is given to a carboxylate mixture formed between pentaerythritol and 2-ethylhexanoic acid/3,5,5-trimethylhexanoic acid and a carboxylate mixture formed between pentaerythritol and 2-ethylpentanoic acid/ 2-methylhexanoic acid/2-ethylhexanoic acid/3,5,5-trimethylhexanoic acid.

In the carboxylate mixture formed between pentaerythritol and 2-ethylhexanoic acid/3,5,5-trimethylhexanoic acid, the mixing ratio of 2-ethylhexanoic acid to 3,5,5-trimethyl hexanoic acid is preferably 80:20 to 35:65 (molar ratio), more preferably 76:24 to 48:52 from the viewpoint of compatibility with hydrofluorocarbons, melting point and viscosity.

In the carboxylate mixture formed between pentaerythritol and 2-ethylpentanoic acid/2-methylhexanoic acid/2-ethylhexanoic acid/3,5,5-trimethylhexanoic acid, the mixing ratio (molar ratio) of the carboxylic acids is preferably 1–12:6–47:5–42:6–72, more preferably 3–10:17–39:5–13:45–72, particularly preferably 3–9:17–35:5–11:50–67 from the viewpoint of compatibility with hydrofluorocarbons, melting point and viscosity.

In a working fluid composition for a refrigerating machine comprising a lubricating oil composition containing an ester compound of the present invention as the main component and hydrofluorocarbons, the mixing ratio of lubricating oil composition to hydrofluorocarbons is not particularly limited, and the ratio of lubricating oil composition/hydrofluorocarbons is preferably 1:50 to 20:1 (weight ratio), more preferably 1:10 to 5:1 (weight ratio). From the viewpoint of achieving a sufficient refrigerating capability, it is desired that the ratio of hydrofluorocarbon is preferably larger than hydrofluorocarbon/lubricating oil composition= 1:20. From the viewpoint of obtaining a working fluid composition for a refrigerating machine with an appropriate viscosity, the ratio of lubricating oil composition is preferably higher than lubricating oil composition/hydrofluorocarbon=1:50.

The hydrofluorocarbons used here are not particularly limited as long as they are conventionally used as a component of a working fluid composition for a refrigerating machine, and preferred examples include difluoromethane (HFC32), 1,1-difluoroethane (HFC152a), 1,1,1-trifluoroethane (HFC143a), 1,1,1,2-tetrafluoroethane (HFC134a), 1,1,2,2-tetrafluoroethane (HFC 134) and pentafluoroethane (HFC125), with particular preference given to difluoromethane, pentafluoroethane, 1,1,1,2-tetrafluoroethane, and 1,1,1-trifluoroethane.

The above hydrofluorocarbons may be used singly or in combination of two or more hydrofluorocarbons.

From the viewpoint of refrigerating efficiency, a hydrofluorocarbon mixture containing difluoromethane (HFC32) is preferred, with particular preference being given to a mixture of difluoromethane, pentafluoroethane and 1,1,1,2-tetrafluoroethane, and a mixture of difluoromethane and pentafluoroethane, and a mixture of difluoromethane and 1,1,1,2-tetrafluoroethane. The most preferable examples of hydrofluorocarbon mixtures are, for example, that comprising 23% by weight of difluoromethane/25% by weight of pentafluoroethane/52% by weight of 1,1,1,2-tetrafluoroethane, or that comprising 40 to 60% by weight of difluoromethane/60 to 40% by weight of pentafluoroethane, though the mixing ratio is not particularly limited.

The ester compound of the present invention has excellent thermal stability in the presence of a metal, and, therefore, the thermal stability of a lubricating oil in the presence of a metal can significantly be increased by blending therewith the ester compound of the present invention. Thus, the present invention further provides methods for increasing the thermal stability in the presence of a metal.

The embodiments of such methods are listed below.

(1) A method for increasing the thermal stability of a lubricating oil in the presence of a metal by using the ester compound of the present invention, as a base oil of the lubricating oil.

(2) A method for increasing the thermal stability of a lubricating oil in the presence of a metal by using the ester compound of the present invention, as a base oil of the lubricating oil composition in an amount of not less than 50% by weight.

(3) A method for increasing the thermal stability of a lubricating oil in the presence of a metal by using a lubricating oil composition containing the ester compound of the present invention as a base oil in the presence of hydrofluorocarbons.

(4) A method for increasing the thermal stability of a lubricating oil in the presence of a metal by using a lubricating oil composition containing the ester compound of the present invention as a base oil in the presence of hydrofluorocarbons containing difluoromethane.

(5) A method for increasing the thermal stability of a lubricating oil in the presence of a metal by using a lubricating oil composition containing the ester compound of the present invention as a base oil in a rotary compressor or a scroll compressor of refrigerating machines.

(6) A method for increasing the thermal stability of a lubricating oil in the presence of a metal by using a lubricating oil composition containing the ester compound of the present invention as a base oil in a compressor of room air conditioners or compressor of packaged air conditioners.

(7) A method for increasing the thermal stability of a lubricating oil in the presence of a metal by using a lubricating oil composition containing the ester compound of the present invention as a base oil, the ester compound of the present invention having a kinematic viscosity at 40° C. of 40 to 90 mm$^2$/s.

(8) A method for increasing the thermal stability of a lubricating oil in the presence of a metal by using a mixture of a lubricating oil composition containing the ester compound of the present invention as a base oil and hydrofluorocarbons where the mixing ratio is adjusted to lubricating oil composition/hydrofluorocarbons=1:50 to 20:1 (weight ratio).

(9) A method for preventing thermal deterioration of a lubricating oil by using the ester compound of the present invention in any one of the above embodiments (1) to (8).

The present invention will be described in further detail by means of the following examples and test examples, without intending to restrict the scope of the present invention thereto.

EXAMPLE 1

A one-liter four-necked flask was equipped with a stirrer, a thermometer, a nitrogen inlet, and a dehydrating column with a condenser. In the flask, 102 g (1.00 mol) of neopentyl glycol, 77.9 g (0.60 mol) of 2-ethylpentanoic acid, and 181.8 g (1.40 mol) of 2-methylhexanoic acid were placed. After the mixture was made to react at 250° C. for 2 hours in a stream of nitrogen at atmospheric pressure, the reaction mixture was subjected to reduced pressure at 20000 Pa for 6 hours. Then, unreacted monocarboxylic acid was distilled away under reduced pressure to obtain ester compound 1 of the present invention. Also, with alcohols and carboxylic acids listed in Tables 1 to 5, the same reaction was carried out to obtain the ester compounds listed in Tables 1 to 5. With these ester compounds, kinematic viscosities at 40° C. and 100° C. and viscosity index were measured (JIS K-2283). Acid value and hydroxyl value were also measured (JIS K-2501). The results are shown in Tables 1 to 5.

TABLE 1

| Ester Compound | Hindered alcohol | Carboxylic acid (Molar No. to 1 mol of hindered alcohol) | | Viscosity at 40° C. (mm²/s) | Viscosity at 100° C. (mm²/s) | Viscosity index | Acid value (mgKOH/g) | Hydroxyl value (mgKOH/g) |
|---|---|---|---|---|---|---|---|---|
| 1 | Neopentyl glycol | 2-Ethylpentanoic acid<br>2-Methylhexanoic acid | (0.60)<br>(1.40) | 5.24 | 1.73 | — | 0.01 | 0.72 |
| 2 | Neopentyl glycol | 2-Ethylhexanoic acid | (2.00) | 7.49 | 2.06 | 52.7 | 0.01 | 1.5 |
| 3 | Neopentyl glycol | 3,5,5-Trimethylhexanoic acid | (2.00) | 13.1 | 3.14 | 100 | 0.01 | 0.35 |
| 4 | Trimethylolpropane | 2-Ethylpentanoic acid<br>2-Methylhexanoic acid | (0.90)<br>(2.10) | 14.9 | 3.34 | 90 | 0.01 | 1.7 |
| 5 | Trimethylolpropane | 2-Ethylhexanoic acid | (3.00) | 25.0 | 4.28 | 55 | 0.01 | 0.11 |
| 6 | Trimethylolpropane | 3,5,5-Trimethylhexanoic acid | (3.00) | 52.1 | 7.19 | 95 | 0.01 | 0.37 |
| 7 | Pentaerythritol | 2-Ethylpentanoic acid<br>2-Methylhexanoic acid | (1.20)<br>(2.80) | 26.8 | 4.89 | 105 | 0.01 | 0.52 |
| 8 | Pentaerythritol | 2-Ethylhexanoic acid | (4.00) | 44.8 | 6.39 | 88 | 0.01 | 0.1 |
| 9 | Pentaerythritol | 3,5,5-Trimethylhexanoic acid | (4.00) | 114.1 | 11.5 | 85 | 0.01 | 1.2 |
| 10 | 2,2-Diethyl-1,3-propanediol | 3,5,5-Trimethylhexanoic acid | (2.00) | 16.9 | 3.74 | 109 | 0.01 | 1.6 |
| 11 | 2-Ethyl-2-n-butyl-1,3-propanediol | 3,5,5-Trimethylhexanoic acid | (2.00) | 21.8 | 4.27 | 100 | 0.01 | 0.30 |
| 12 | Trimethylolpropane | 2-Ethylhexanoic acid<br>3,5,5-Trimethylhexanoic acid | (1.56)<br>(1.44) | 32.5 | 5.13 | 78 | 0.01 | 1.3 |

TABLE 2

| Ester compound | Hindered alcohol | Carboxylic acid (Molar No. to 1 mol of hindered alcohol) | | Viscosity at 40° C. (mm²/s) | Viscosity at 100° C. (mm²/s) | Viscosity index | Acid value (mgKOH/g) | Hydroxyl value (mgKOH/g) |
|---|---|---|---|---|---|---|---|---|
| 13 | Pentaerythritol | 2-Ethylhexanoic acid<br>3,5,5-Trimethylhexanoic acid | (2.45)<br>(1.55) | 61.8 | 7.94 | 93 | 0.01 | 1.8 |
| 14 | Pentaerythritol | 2-Ethylhexanoic acid<br>3,5,5-Trimethylhexanoic acid | (1.93)<br>(2.07) | 70.2 | 8.63 | 93 | 0.01 | 2.4 |
| 15 | Trimethylolpropane | 2-Ethylpentanoic acid<br>2-Methylhexanoic acid<br>2-Ethylhexanoic acid | (0.46)<br>(1.99)<br>(0.55) | 16.0 | 3.45 | 83 | 0.01 | 1.5 |
| 16 | Pentaerythritol | 2-Ethylpentanoic acid<br>2-Methylhexanoic acid<br>2-Ethylhexanoic acid | (0.44)<br>(1.92)<br>(1.64) | 30.7 | 5.19 | 97 | 0.01 | 4.8 |
| 17 | Trimethylolpropane | 2-Ethylpentanoic acid<br>2-Methylhexanoic acid<br>2-Ethylhexanoic acid<br>3,5,5-Trimethylhexanoic acid | (0.19)<br>(0.82)<br>(0.23)<br>(1.76) | 31.5 | 5.33 | 122 | 0.01 | 1.4 |
| 18 | Pentaerythritol | 2-Ethylpentanoic acid<br>2-Methylhexanoic acid<br>2-Ethylhexanoic acid<br>3,5,5-Trimethylhexanoic acid | (0.22)<br>(0.51)<br>(1.79)<br>(1.48) | 54.3 | 7.35 | 94 | 0.01 | 2.8 |
| 19 | Pentaerythritol | 2-Ethylpentanoic acid<br>2-Methylhexanoic acid<br>2-Ethylhexanoic acid<br>3,5,5-Trimethylhexanoic acid | (0.06)<br>(0.27)<br>(1.54)<br>(2.13) | 68.3 | 8.46 | 92 | 0.01 | 1.9 |

TABLE 3

| Ester compound | Hindered alcohol | Carboxylic acid (Molar No. to 1 mol of hindered alcohol) | | Viscosity at 40° C. (mm²/s) | Viscosity at 100° C. (mm²/s) | Viscosity index | Acid value (mgKOH/g) | Hydroxyl value (mgKOH/g) |
|---|---|---|---|---|---|---|---|---|
| 20 | Pentaerythritol | n-Heptanoic acid<br>3,5,5-Trimethylhexanoic acid | (0.36)<br>(3.64) | 94.9 | 10.5 | 92 | 0.01 | 0.88 |
| 21 | Pentaerythritol | n-Heptanoic acid<br>3,5,5-Trimethylhexanoic acid | (0.76)<br>(3.24) | 78.5 | 9.35 | 94 | 0.01 | 0.97 |
| 22 | Pentaerythritol | n-Octanoic acid<br>3,5,5-Trimethylhexanoic acid | (0.48)<br>(3.52) | 91.1 | 10.1 | 89 | 0.01 | 2.1 |
| 23 | Pentaerythritol | n-Octanoic acid<br>3,5,5-Trimethylhexanoic acid | (0.72)<br>(3.28) | 83.5 | 9.79 | 95 | 0.01 | 1.2 |

TABLE 3-continued

| Ester compound | Hindered alcohol | Carboxylic acid (Molar No. to 1 mol of hindered alcohol) | | Viscosity at 40° C. (mm$^2$/s) | Viscosity at 100° C. (mm$^2$/s) | Viscosity index | Acid value (mgKOH/g) | Hydroxyl value (mgKOH/g) |
|---|---|---|---|---|---|---|---|---|
| 24 | Pentaerythritol | 2-Ethylhexanoic acid | (1.93) | 70.2 | 8.62 | 93 | 0.05 | 2.4 |
|  |  | 3,5,5-Trimethylhexanoic acid | (2.07) |  |  |  |  |  |
| 25 | Pentaerythritol | 2-Ethylhexanoic acid | (1.93) | 70.1 | 8.64 | 93 | 0.10 | 2.4 |
|  |  | 3,5,5-Trimethylhexanoic acid | (2.07) |  |  |  |  |  |
| 26 | Pentaerythritol | 2-Ethylhexanoic acid | (1.93) | 70.9 | 8.62 | 91 | 0.01 | 9.8 |
|  |  | 3,5,5-Trimethylhexanoic acid | (2.07) |  |  |  |  |  |
| 27 | Pentaerythritol | 2-Ethylhexanoic acid | (1.93) | 71.5 | 8.65 | 91 | 0.01 | 14.3 |
|  |  | 3,5,5-Trimethylhexanoic acid | (2.07) |  |  |  |  |  |
| 28 | Pentaerythritol | 2-Ethylpentanoic acid | (0.26) | 60.4 | 8.01 | 98 | 0.01 | 2.0 |
|  |  | 2-Methylhexanoic acid | (1.16) |  |  |  |  |  |
|  |  | 2-Ethylhexanoic acid | (0.35) |  |  |  |  |  |
|  |  | 3,5,5-Trimethylhexanoic acid | (2.23) |  |  |  |  |  |
| a | Pentaerythritol | 2-Ethylhexanoic acid | (1.93) | 73.0 | 8.60 | 86 | 0.01 | 25.1 |
|  |  | 3,5,5-Trimethylhexanoic acid | (2.07) |  |  |  |  |  |
| b | Pentaerythritol | 2-Ethylhexanoic acid | (1.93) | 73.5 | 8.54 | 83 | 0.01 | 32.5 |
|  |  | 3,5,5-Trimethylhexanoic acid | (2.07) |  |  |  |  |  |
| c | Pentaerythritol | n-Heptanoic acid | (0.40) | 64.3 | 8.34 | 98 | 0.01 | 0.75 |
|  |  | 2-Ethylhexanoic acid | (1.44) |  |  |  |  |  |
|  |  | 3,5,5-Trimethylhexanoic acid | (2.16) |  |  |  |  |  |
| d | Pentaerythritol | n-Heptanoic acid | (0.40) | 67.0 | 8.45 | 95 | 0.01 | 11.5 |
|  |  | 2-Ethylhexanoic acid | (1.44) |  |  |  |  |  |
|  |  | 3,5,5-Trimethylhexanoic acid | (2.16) |  |  |  |  |  |
| e | Pentaerythritol | n-Heptanoic acid | (0.40) | 68.9 | 8.53 | 92 | 0.01 | 23.1 |
|  |  | 2-Ethylhexanoic acid | (1.44) |  |  |  |  |  |
|  |  | 3,5,5-Trimethylhexanoic acid | (2.16) |  |  |  |  |  |
| f | Pentaerythritol | n-Heptanoic acid | (0.40) | 72.0 | 8.73 | 92 | 0.01 | 36.5 |
|  |  | 2-Ethylhexanoic acid | (1.44) |  |  |  |  |  |
|  |  | 3,5,5-Trimethylhexanoic acid | (2.16) |  |  |  |  |  |
| g | Pentaerythritol | n-Pentanoic acid | (0.63) | 63.9 | 8.23 | 96 | 0.01 | 5.3 |
|  |  | 2-Methylbutyric acid | (0.31) |  |  |  |  |  |
|  |  | 3,5,5-Trimethylhexanoic acid | (3.06) |  |  |  |  |  |
| h | Pentaerythritol | n-Pentanoic acid | (0.63) | 64.4 | 8.20 | 94 | 0.01 | 12.1 |
|  |  | 2-Methylbutyric acid | (0.31) |  |  |  |  |  |
|  |  | 3,5,5-Trimethylhexanoic acid | (3.06) |  |  |  |  |  |
| i | Pentaerythritol | n-Pentanoic acid | (0.63) | 65.7 | 8.15 | 90 | 0.01 | 28.3 |
|  |  | 2-Methylbutyric acid | (0.31) |  |  |  |  |  |
|  |  | 3,5,5-Trimethylhexanoic acid | (3.06) |  |  |  |  |  |
| j | Pentaerythritol | n-Heptanoic acid | (0.98) | 69.0 | 9.01 | 105 | 0.01 | 8.7 |
|  |  | 3,5,5-Trimethylhexanoic acid | (3.02) |  |  |  |  |  |
| k | Pentaerythritol | n-Heptanoic acid | (0.98) | 69.5 | 8.96 | 102 | 0.01 | 19.5 |
|  |  | 3,5,5-Trimethylhexanoic acid | (3.02) |  |  |  |  |  |
| l | Pentaerythritol | n-Heptanoic acid | (0.98) | 72.0 | 8.90 | 96 | 0.01 | 41.7 |
|  |  | 3,5,5-Trimethylhexanoic acid | (3.02) |  |  |  |  |  |
| m | Pentaerythritol | n-Octanoic acid | (1.37) | 56.3 | 8.01 | 110 | 0.01 | 13.8 |
|  |  | 3,5,5-Trimethylhexanoic acid | (2.63) |  |  |  |  |  |
| n | Pentaerythritol | n-Octanoic acid | (1.37) | 57.9 | 7.98 | 104 | 0.01 | 26.7 |
|  |  | 3,5,5-Trimethylhexanoic acid | (2.63) |  |  |  |  |  |
| o | Pentaerythritol | n-Heptanoic acid | (1.80) | 45.4 | 6.98 | 111 | 0.01 | 0.35 |
|  |  | 3,5,5-Trimethylhexanoic acid | (2.20) |  |  |  |  |  |
| p | Pentaerythritol | n-Heptanoic acid | (1.80) | 46.1 | 6.95 | 107 | 0.01 | 18.1 |
|  |  | 3,5,5-Trimethylhexanoic acid | (2.20) |  |  |  |  |  |
| q | Pentaerythritol | 2-Ethylhexanoic acid | (1.93) | 76.1 | 8.38 | 73 | 0.01 | 53.0 |
|  |  | 3,5,5-Trimethylhexanoic acid | (2.07) |  |  |  |  |  |
| r | Pentaerythritol | n-Heptanoic acid | (0.40) | 77.4 | 8.70 | 80 | 0.01 | 51.1 |
|  |  | 2-Ethylhexanoic acid | (1.44) |  |  |  |  |  |
|  |  | 3,5,5-Trimethylhexanoic acid | (2.16) |  |  |  |  |  |
| s | Pentaerythritol | n-Pentanoic acid | (0.63) | 68.0 | 8.03 | 80 | 0.01 | 54.2 |
|  |  | 2-Methylbutyric acid | (0.31) |  |  |  |  |  |
|  |  | 3,5,5-Trimethylhexanoic acid | (3.06) |  |  |  |  |  |
| t | Pentaerythritol | n-Pentanoic acid | (2.24) | 32.9 | 5.31 | 90 | 0.01 | 52.8 |
|  |  | 3,5,5-Trimethylhexanoic acid | (1.76) |  |  |  |  |  |
| u | Pentaerythritol | n-Heptanoic acid | (1.80) | 47.2 | 6.92 | 102 | 0.01 | 34.4 |
|  |  | 3,5,5-Trimethylhexanoic acid | (2.20) |  |  |  |  |  |
| v | Pentaerythritol | n-Octanoic acid | (2.00) | 53.1 | 7.79 | 112 | 0.01 | 2.2 |
|  |  | 3,5,5-Trimethylhexanoic acid | (2.00) |  |  |  |  |  |

TABLE 4

| Ester compound | Hindered alcohol | Carboxylic acid (Molar No. to 1 mol of hindered alcohol) | | Viscosity at 40° C. (mm²/s) | Viscosity at 100° C. (mm²/s) | Viscosity index | Acid value (mgKOH/g) | Hydroxyl value (mgKOH/g) |
|---|---|---|---|---|---|---|---|---|
| A | Neopentyl glycol | n-Heptanoic acid | (2.00) | 5.62 | 1.89 | — | 0.01 | 0.43 |
| B | Neopentyl glycol | n-Octanoic acid | (2.00) | 7.03 | 2.23 | 133 | 0.01 | 1.0 |
| C | Trimethylolpropane | n-Heptanoic acid | (3.00) | 13.8 | 3.40 | 122 | 0.01 | 1.8 |
| D | Trimethylolpropane | n-Octanoic acid | (3.00) | 17.0 | 4.03 | 140 | 0.01 | 0.67 |
| | Pentaerythritol | n-Heptanoic acid | (4.00) | 22.3 | 4.74 | 136 | 0.01 | 4.9 |
| F | Pentaerythritol | n-Octanoic acid | (4.00) | 26.7 | 5.42 | 143 | 0.01 | 0.74 |
| G | Pentaerythritol | n-Heptanoic acid | (1.37) | 56.1 | 8.04 | 111 | 0.01 | 1.3 |
| | | 3,5,5-Trimethylhexanoic acid | (2.63) | | | | | |
| H | Pentaerythritol | n-Heptanoic acid | (0.98) | 68.8 | 9.00 | 105 | 0.01 | 1.1 |
| | | 3,5,5-Trimethylhexanoic acid | (3.02) | | | | | |
| I | Pentaerythritol | n-Octanoic acid | (1.49) | 55.3 | 8.10 | 115 | 0.01 | 1.5 |
| | | 3,5,5-Trimethylhexanoic acid | (2.51) | | | | | |
| J | Pentaerythritol | n-Octanoic acid | (0.99) | 67.2 | 8.90 | 106 | 0.01 | 2.1 |
| | | 3,5,5-Trimethylhexanoic acid | (3.01) | | | | | |
| K | Pentaerythritol | 2-Ethylhexanoic acid | (1.93) | 70.2 | 8.63 | 93 | 0.20 | 2.4 |
| | | 3,5,5-Trimethylhexanoic acid | (2.07) | | | | | |

TABLE 5

| Ester compound | Hindered alcohol | Carboxylic acid (Molar No. to 1 mol of hindered alcohol) | | Viscosity at 40° C. (mm²/s) | Viscosity at 100° C. (mm²/s) | Viscosity index | Acid value (mgKOH/g) | Hydroxyl value (mgKOH/g) |
|---|---|---|---|---|---|---|---|---|
| L | Pentaerythritol | 2-Ethylhexanoic acid | (1.93) | 72.1 | 8.60 | 88 | 0.01 | 17.6 |
| | | 3,5,5-Trimethylhexanoic acid | (2.07) | | | | | |
| M | Pentaerythritol | n-Pentanoic acid | (2.24) | 30.4 | 5.46 | 116 | 0.01 | 3.2 |
| | | 3,5,5-Trimethylhexanoic acid | (1.76) | | | | | |
| N | Pentaerythritol | n-Pentanoic acid | (2.23) | 22.7 | 4.50 | 119 | 0.01 | 3.5 |
| | | 2-Methylbutyric acid | (0.90) | | | | | |
| | | 3,5,5-Trimethylhexanoic acid | (0.87) | | | | | |
| O | Pentaerythritol | n-Pentanoic acid | (0.83) | 56.7 | 7.81 | 102 | 0.01 | 3.0 |
| | | 2-Methylbutyric acid | (0.45) | | | | | |
| | | 3,5,5-Trimethylhexanoic acid | (2.72) | | | | | |

TEST EXAMPLE 1

With the ester compounds obtained in Example 1, a thermal stability test was carried out under the following conditions in order to evaluate the thermal stability in the presence of a metal in both cases where the carboxylic acid moiety is branched and where the carboxylic acid moiety is linear with no branches. Specifically, 10 g of an inventive product or a comparative product, which had been adjusted to have a water content of 10 ppm in advance and sufficiently degassed, was placed in a glass vessel with an inner diameter of 15 mm, length of 170 mm and inner volume of about 30 ml, in which an iron wire having a diameter of 1.6 mm and a length of 150 mm was placed as a piece of metal. Then, the pressure inside the vessel was reduced to not higher than 1.3 Pa and the vessel was sealed. After the test was continued at 250° C. for 3 days, the acid value of the ester compound was measured. The results are shown in Table 6.

As obvious from Table 6, the thermal stability of linear carboxylates, the comparative products, is poor in the presence of a metal with a significant increase in acid value as compared with the system where no metals were present. On the contrary, the branched carboxylates of the present invention showed substantially no increase in acid value even in the presence of a metal, demonstrating excellent thermal stability.

TABLE 6

| | Ester compound | Metal piece (iron wire) | Acid value of oil after thermal stability test (mgKOH/g) |
|---|---|---|---|
| Present Inventive Product | 8 | Existed | 1.2 |
| Comparative Product | F | Existed | 36.6 |
| | | Not existed | 1.4 |

TEST EXAMPLE 2

With the ester compounds obtained in Example 1 (the present inventive products and comparative products), a thermal stability test was carried out under the conditions as shown in Test Example 1 in order to further evaluate thermal stability in the presence of a metal in both cases where the carboxylic acid moiety is branched and where the carboxylic acid moiety is linear with no branches. The results are shown in Table 7.

TABLE 7

| | Ester compound | Acid value of oil after thermal stability test (mgKOH/g) |
|---|---|---|
| Present Inventive Product | 1 | 1.5 |
| | 2 | 0.24 |
| | 3 | 0.88 |
| | 4 | 3.9 |
| | 5 | 0.68 |
| | 6 | 2.0 |
| | 7 | 6.7 |
| | 8 | 1.2 |
| | 9 | 3.3 |
| | 10 | 0.71 |
| | 11 | 0.54 |
| Comparative Product | A | 37.2 |
| | B | 15.2 |
| | C | 65.4 |
| | D | 22.9 |
| | E | 89.0 |
| | F | 36.6 |

As obvious from Table 7, the present inventive products prepared using branched carboxylic acids showed less increase in acid value after the test as compared with the comparative products prepared using linear carboxylic acid, clearly demonstrating excellent thermal stability in the presence of a metal.

TEST EXAMPLE 3

With the ester compounds obtained in Example 1, a thermal stability test was carried out under the conditions shown in Test Example 1 in order to evaluate the influence of branched ratio on thermal stability and the influence of the other properties of the ester compounds on thermal stability. The results are shown in Table 8.

As obvious from Table 8, ester compounds with a branched ratio of not lower than 80 mol % show better thermal stability in the presence of a metal with showing less increase in acid value, as compared with ester compounds having a branched ratio of lower than 80 mol %. Also, when hydroxyl value of ester compounds before the test was not higher than 15 mg KOH/g, the increase in acid value after the test was suppressed, demonstrating good thermal stability in the presence of a metal. Also, there observed a tendency that the higher the acid value of ester compounds before the test, the higher the acid value after the test.

TABLE 8

| Ester compound | Branched ratio (%) | Initial acid value (mgKOH/g) | Initial hydroxyl value (mgKOH/g) | Acid value of oil after thermal stability test (mgKOH/g) |
|---|---|---|---|---|
| 6 | 100 | 0.01 | 0.37 | 2.0 |
| 12 | 100 | 0.01 | 1.3 | 1.4 |
| 13 | 100 | 0.01 | 1.8 | 2.2 |
| 14 | 100 | 0.01 | 2.4 | 2.6 |
| 15 | 100 | 0.01 | 1.5 | 3.5 |
| 16 | 100 | 0.01 | 4.8 | 4.0 |
| 17 | 100 | 0.01 | 1.4 | 2.7 |
| 18 | 100 | 0.01 | 2.8 | 3.3 |
| 19 | 100 | 0.01 | 1.9 | 3.7 |
| 28 | 100 | 0.01 | 2.0 | 3.6 |
| 20 | 91 | 0.01 | 0.88 | 5.5 |
| 22 | 88 | 0.01 | 2.1 | 4.1 |
| 23 | 82 | 0.01 | 1.2 | 5.9 |
| 21 | 81 | 0.01 | 0.97 | 7.4 |
| O | 79 | 0.01 | 3.0 | 25.7 |
| H | 76 | 0.01 | 1.1 | 18.2 |
| J | 75 | 0.01 | 2.1 | 29.5 |
| G | 66 | 0.01 | 1.3 | 22.5 |
| I | 63 | 0.01 | 1.5 | 32.3 |
| 26 | 100 | 0.01 | 9.8 | 3.8 |
| 27 | 100 | 0.01 | 14.3 | 9.2 |
| a | 100 | 0.01 | 25.1 | 11.5 |
| b | 100 | 0.01 | 32.5 | 24.6 |
| c | 90 | 0.01 | 0.75 | 3.9 |
| d | 90 | 0.01 | 11.5 | 8.7 |
| e | 90 | 0.01 | 23.1 | 21.1 |
| g | 84 | 0.01 | 5.3 | 9.9 |
| h | 84 | 0.01 | 12.1 | 9.8 |
| 24 | 100 | 0.05 | 2.4 | 4.7 |
| 25 | 100 | 0.1 | 2.4 | 8.5 |
| K | 100 | 0.02 | 2.4 | 17.9 |
| L | 100 | 0.01 | 17.6 | 21.9 |
| M | 44 | 0.01 | 3.2 | 50< |
| N | 44 | 0.01 | 3.5 | 50< |

TEST EXAMPLE 4

With the ester compounds obtained in Example 1, the performance as a working fluid composition for a refrigerating machine was evaluated. A low temperature at which two-phase separation occurs between a mixture of difluoromethane (HFC32)/pentafluoroethane (HFC125)=50:50 (weight ratio) or a mixture of difluoromethane/pentafluoroethane/1,1,1,2-tetrafluoroethane (HFC134a)= 23:25:52 (weight ratio) and an ester compound (ester compound/hydrofluorocarbon=30:70, weight ratio) was measured. The results are shown in Table 9.

TABLE 9

| Ester compound | Branched ratio (%) | Hydroxyl value (mgKOH/g) | Phase-separation temperature (° C.) | | Acid value of oil after sealed tube test (mgKOH/g) | | | |
|---|---|---|---|---|---|---|---|---|
| | | | HFC32/125 | HFC32/125/134a | HFC32/125/134a 250° C. 3 days | HFC32/125/134a 175° C. 14 days | HFC32/125 175° C. 14 days | HFC134a 175° C. 14 days |
| 6 | 100 | 0.37 | −18 | −30 > | 0.6 | 0.03 > | 0.03 > | 0.03 > |
| 12 | 100 | 1.3 | −14 | −30 > | 0.5 | 0.03 > | 0.03 > | 0.03 > |
| 13 | 100 | 1.8 | +4 | −14 | 0.7 | 0.03 > | 0.03 > | 0.03 > |
| 14 | 100 | 2.4 | +2 | −15 | 0.7 | 0.03 > | 0.03 > | 0.03 > |
| 15 | 100 | 1.5 | −30 > | −30 > | 0.6 | 0.03 > | 0.03 > | 0.03 > |
| 16 | 100 | 4.8 | −21 | −30 > | 0.6 | 0.03 > | 0.03 > | 0.03 > |
| 17 | 100 | 1.4 | −28 | −30 > | 0.6 | 0.03 > | 0.03 > | 0.03 > |
| 18 | 100 | 2.8 | −6 | −20 | 0.7 | 0.03 > | 0.03 > | 0.03 > |

TABLE 9-continued

| Ester compound | Branched ratio (%) | Hydroxyl value (mgKOH/g) | Phase-separation temperature (° C.) HFC32/125 | Phase-separation temperature (° C.) HFC32/125/134a | Acid value of oil after sealed tube test (mgKOH/g) HFC32/125/134a 250° C. 3 days | Acid value of oil after sealed tube test (mgKOH/g) HFC32/125/134a 175° C. 14 days | Acid value of oil after sealed tube test (mgKOH/g) HFC32/125 175° C. 14 days | Acid value of oil after sealed tube test (mgKOH/g) HFC134a 175° C. 14 days |
|---|---|---|---|---|---|---|---|---|
| 19 | 100 | 1.9 | −1 | −19 | 0.7 | 0.03 > | 0.03 > | 0.03 > |
| 28 | 100 | 2.0 | −9 | −24 | 0.6 | 0.03 > | 0.03 > | 0.03 > |
| 26 | 100 | 9.8 | +5 | −13 | 0.8 | 0.03 > | 0.03 > | 0.03 > |
| 27 | 100 | 14.3 | +6 | −11 | 0.8 | 0.03 > | 0.03 > | 0.03 > |
| L | 100 | 17.6 | +8 | −10 | 0.9 | 0.03 > | 0.03 > | 0.03 > |
| a | 100 | 25.1 | +10 | −7 | 2.8 | 0.03 > | 0.03 > | 0.03 > |
| b | 100 | 32.5 | +10 < | −5 | 6.3 | 0.03 > | 0.03 > | 0.03 > |
| c | 90 | 0.75 | +5 | −13 | 0.8 | 0.03 > | 0.03 > | 0.03 > |
| d | 90 | 11.5 | +8 | −11 | 1.1 | 0.03 > | 0.03 > | 0.03 > |
| e | 90 | 23.1 | +10 < | −7 | 4.5 | 0.03 > | 0.03 > | 0.03 > |
| f | 90 | 36.5 | +10 < | −3 | 11.4 | 0.03 > | 0.03 > | 0.03 > |
| g | 84 | 5.3 | −30 | −30 > | 1.0 | 0.03 > | 0.03 > | 0.03 > |
| h | 84 | 12.1 | −26 | −30 > | 1.7 | 0.03 > | 0.03 > | 0.03 > |
| i | 84 | 28.3 | −20 | −30 > | 8.5 | 0.03 > | 0.03 > | 0.03 > |
| O | 79 | 3.0 | −30 | −30 > | 0.9 | 0.03 > | 0.03 > | 0.03 > |
| H | 76 | 1.1 | +1 | −15 | 0.8 | 0.03 > | 0.03 > | 0.03 > |
| j | 76 | 8.7 | +4 | −13 | 2.0 | 0.03 > | 0.03 > | 0.03 > |
| k | 76 | 19.5 | +7 | −9 | 5.5 | 0.03 > | 0.03 > | 0.03 > |
| l | 76 | 41.7 | +10 < | 0 | 37.8 | 0.03 > | 0.03 > | 0.03 > |
| J | 75 | 2.1 | +10 < | 0 | 1.1 | 0.03 > | 0.03 > | 0.03 > |
| G | 66 | 1.3 | +7 | −12 | 1.2 | 0.03 > | 0.03 > | 0.03 > |
| m | 66 | 13.8 | +8 | −10 | 5.1 | 0.03 > | 0.03 > | 0.03 > |
| n | 66 | 26.7 | +10 < | −6 | 9.4 | 0.03 > | 0.03 > | 0.03 > |
| I | 63 | 1.5 | +10 < | +10 < | 1.6 | 0.03 > | 0.03 > | 0.03 > |
| o | 55 | 0.35 | +10 < | −8 | 2.0 | 0.03 > | 0.03 > | 0.03 > |
| p | 55 | 18.1 | +10 < | 0 | 8.3 | 0.03 > | 0.03 > | 0.03 > |
| M | 44 | 3.2 | −30 > | −30 > | 3.2 | 0.03 > | 0.03 > | 0.03 > |
| N | 44 | 3.5 | −30 > | −30 > | 3.3 | 0.03 > | 0.03 > | 0.03 > |
| q | 100 | 53.0 | +10 < | +2 | 15.6 | 0.03 > | 0.03 > | 0.03 > |
| r | 90 | 51.1 | +10 < | +2 | 21.3 | 0.03 > | 0.03 > | 0.03 > |
| s | 84 | 54.2 | −8 | −26 | 29.1 | 0.03 > | 0.03 > | 0.03 > |
| t | 44 | 52.8 | +10 < | +10 < | 73.8 | 0.03 > | 0.03 > | 0.03 > |
| u | 55 | 34.4 | +10 < | 1 | 29.4 | 0.03 > | 0.03 > | 0.03 > |

TEST EXAMPLE 5

A sealed tube test was carried out with the ester compound of the present invention.

After the water content of the ester compound in an amount of 5 g was adjusted to not more than 10 ppm, the ester compound was placed in a glass vessel with an inner volume of 15 ml along with iron, copper and aluminum pieces each having a diameter of 1.6 mm and a length of 100 mm. After the inside of the vessel was degassed to not higher than 1.3 Pa, 1 g of a mixture of difluoromethane/pentafluoroethane/1,1,1,2-tetrafluoroethane=23:25:52 (weight ratio) was placed in the vessel, and then the vessel was sealed. After the vessel was allowed to stand at 250° C. for 3 days, the vessel was opened. After the mixture was removed, acid value of the ester compound was measured. The results are shown in Table 9.

Figure 2:
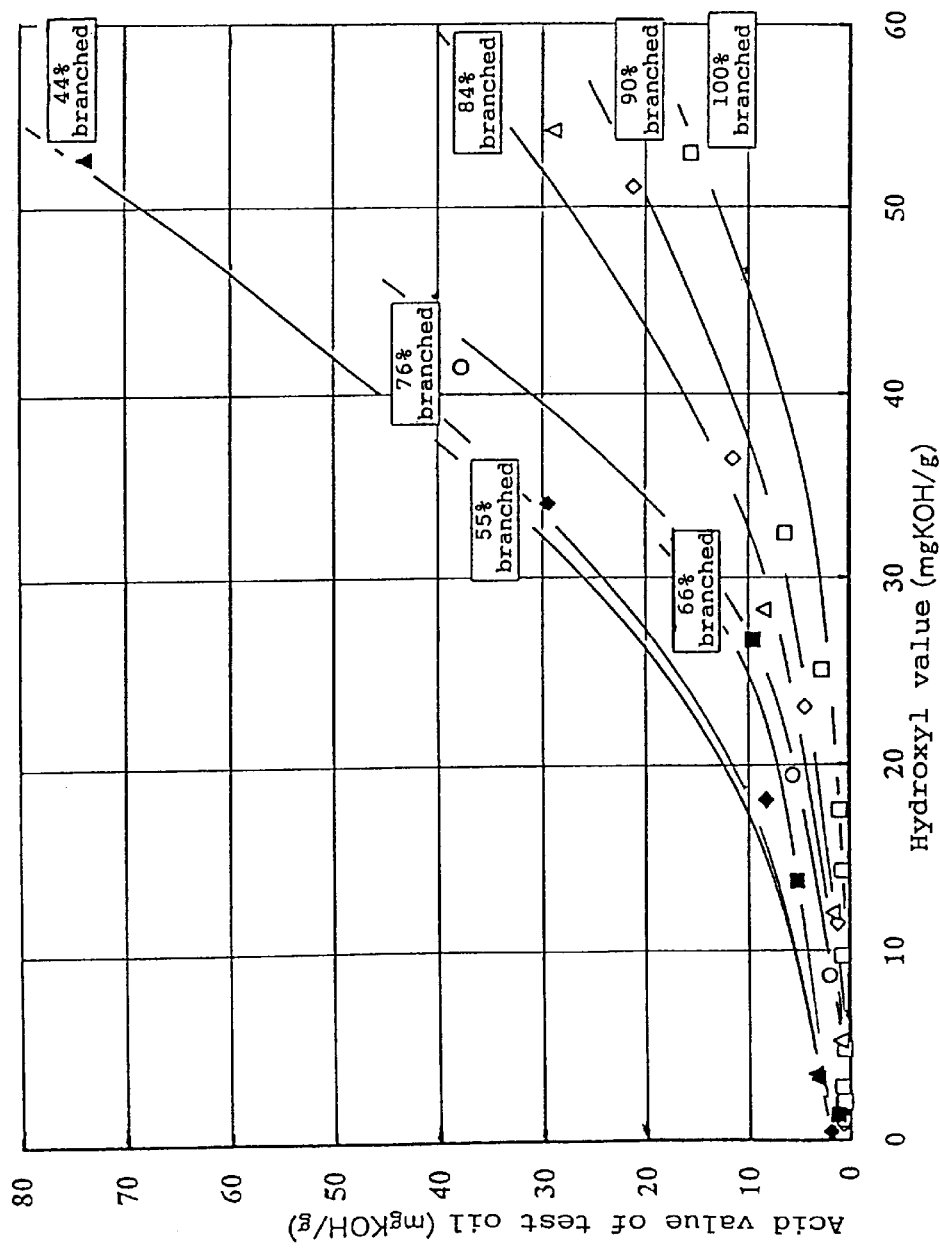
FIG. 2 is a graph which shows the relation between hydroxyl value/branched ratio and acid value after a sealed tube test of ester compounds. The horizontal axis is the hydroxyl value of an ester compound, and the vertical axis is acid value measured after a sealed tube test. In the graph, ▲ is the data of an ester compound having a branched ratio of 44 mol %, ♦ is the data of an ester compound having a branched ratio of 55 mol %, ■ is the data of an ester compound having a branched ratio of 66 mol %, ○ is the data of an ester compound having a branched ratio of 76 mol %, Δ is the data of an ester compound having a branched ratio of 84 mol %, ◊ is the data of an ester compound having a branched ratio of 90 mol %, and □ is the data of an ester compound having a branched ratio of 100 mol %.
Figure 3:
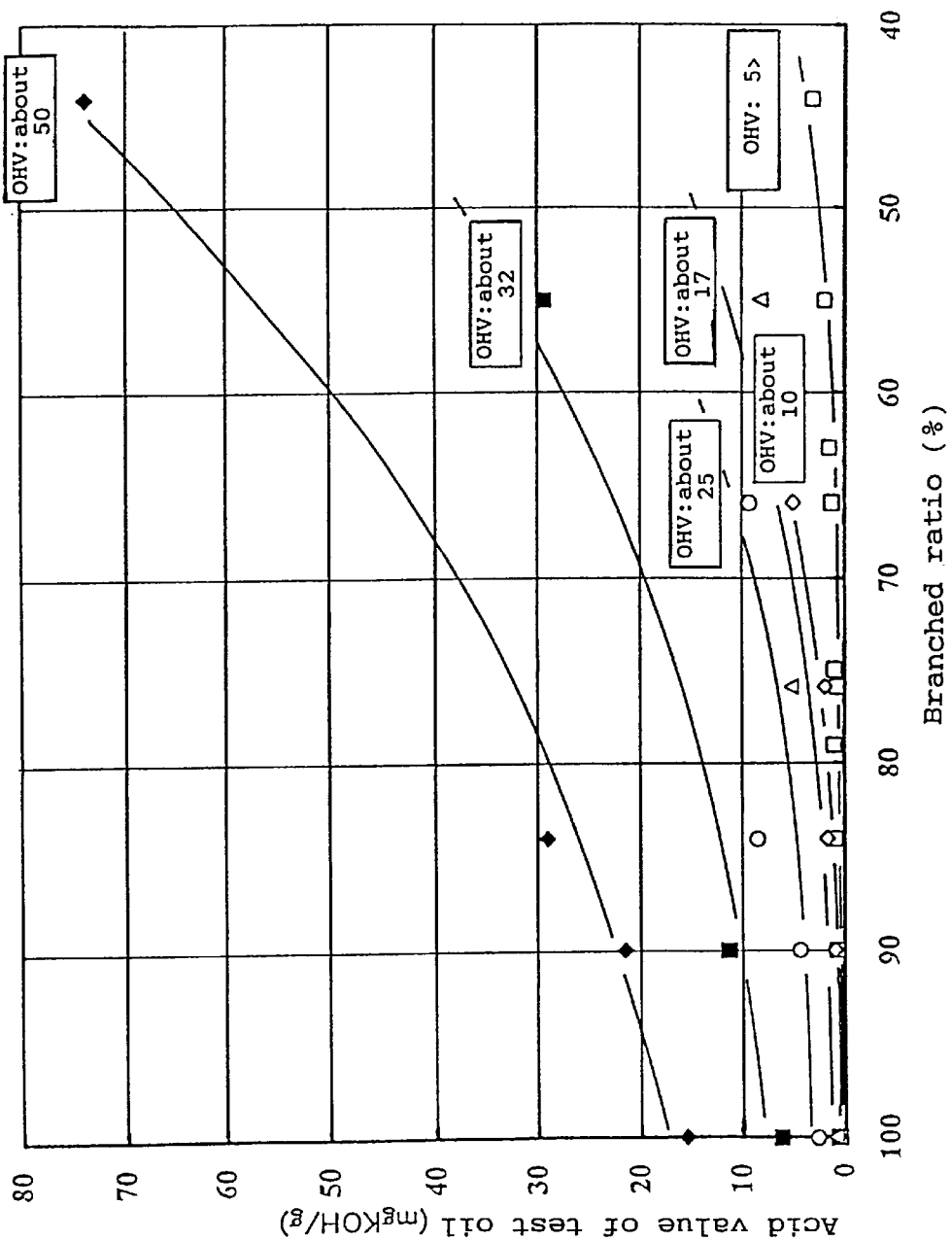
FIG. 3 is a graph which shows the relation between hydroxyl value/branched ratio and acid value after a sealed tube test of ester compounds. The horizontal axis is branched ratio of an ester compound and the vertical axis is acid value measured after a sealed tube test. In the graph, ♦ is the data of an ester compound having a hydroxyl value of about 50 mg KOH/g, ■ is the data of an ester compound having a hydroxyl value of about 32 mg KOH/g, ○ is the data of an ester compound having a hydroxyl value of about 25 mg KOH/g, Δ is the data of an ester compound having a hydroxyl value of about 17 mg KOH/g, ◊ is the data of an ester compound having a hydroxyl value of about 10 mg KOH/g, and □ is the data of an ester compound having a hydroxyl value of not more than about 5 mg KOH/g.
Figure 4:
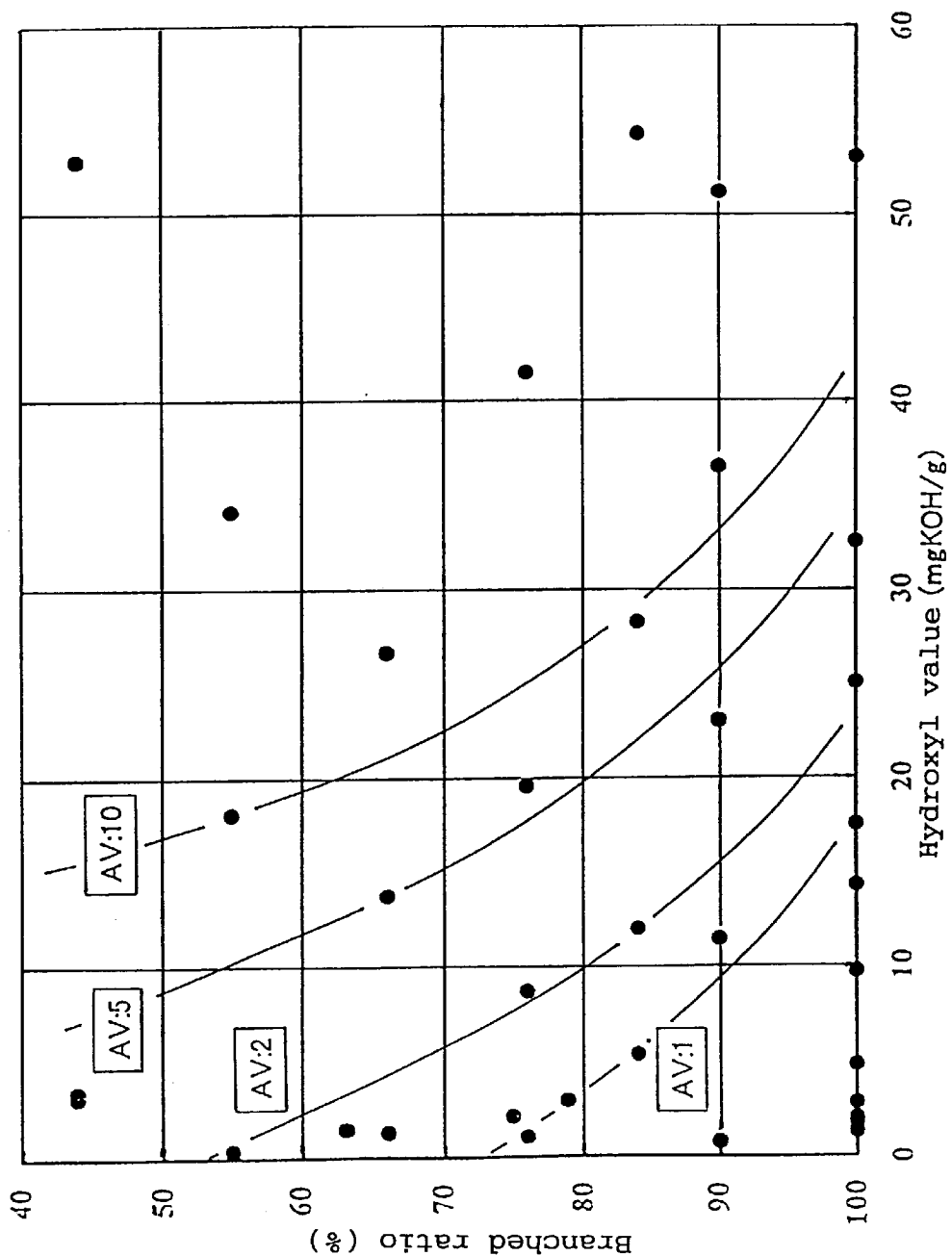
FIG. 4 is a graph which shows the relation between hydroxyl value/branched ratio and acid value (AV) after a sealed tube test of ester compounds. The horizontal axis is hydroxyl value of ester compounds and the vertical axis is branched ratio of ester compounds.

Also, graphs showing the relation of hydroxyl value, branched ratio and acid value measured after a sealed tube test of the ester compounds are shown in FIGS. 2, 3 and 4.

From Table 9 and the graphs in FIGS. 2 to 4, ester compounds having a branched ratio of not lower than 50 mol % and a hydroxyl value of not higher than 30 mg KOH/g, in particular those having a branched ratio of not lower than 70 mol % and a hydroxyl value of not higher than 20 mg KOH/g, those having a branched ratio of not lower than 50 mol % and a hydroxyl value of not higher than 10 mg KOH/g and those having a branched ratio of not lower than 90 mol % and a hydroxyl value of not higher than 30 mg KOH/g were found to have remarkably good thermal stability in the presence of a metal.

For reference, the results obtained after the above sealed tube test was carried out at 175° C. for 14 days with a mixture of difluoromethane/pentafluoroethane/1,1,1,2-tetrafluoroethane=23:25:52 (weight ratio) or with a mixture of difluoromethane/pentafluoroethane =50:50 (weight ratio), and the results obtained after the test was carried out at 175° C. for 14 days with 1,1,1,2-tetrafluoroethane are together listed in Table 9.

From Table 9, it is found that the thermal stability is good regardless of the branched ratio and hydroxyl value of ester compounds under the conditions of 175° C. for 14 days.

TEST EXAMPLE 6

Next, the wear amount was measured using a high-pressure wear tester (manufactured by Shinko Engineering Co., Ltd.) in order to evaluate the lubricity of a working fluid composition for a refrigerating machine containing the ester compound of the present invention.

In a test vessel, 480 g of an ester compound and 240 g of a mixture of difluoromethane/pentafluoroethane=50:50 (weight ratio) were placed, and kept at 100° C. Using a vane and a disc as the test pieces, a test was carried out with a load of 200 kg at 500 rpm for 6 hours and the wear amounts of the vane and the disc were determined. The results are shown in Table 10. The working fluid composition for a refrigerating machine using an ester compound having a kinematic viscosity at 40° C. of not lower than 40 mm²/s has a better wear resistance than that using an ester compound having a kinematic viscosity of lower than 40 mm²/s.

TABLE 10

| Ester compound | Viscosity of ester compound at 40° C. (mm²/s) | Wear amount (mg) |
| --- | --- | --- |
| 13 | 61.8 | 14.5 |
| 14 | 70.2 | 12.4 |
| 28 | 60.4 | 14.9 |
| 19 | 68.3 | 13.1 |
| 6 | 52.1 | 19.8 |
| 12 | 32.5 | 28.3 |
| 16 | 30.7 | 29.8 |
| 17 | 31.5 | 30.4 |
| 15 | 16.0 | 36.5 |

TEST EXAMPLE 7

Next, with working fluid compositions for a refrigerating machine using the ester compound of the present invention, wear amount of a vane and acid value of the ester compound were evaluated using a commercially available rotary compressor for room air conditioners.

In a rotary compressor, 450 g of an ester compound of which water content had previously been adjusted to not higher than 20 ppm and 160 g of a mixture of difluoromethane/pentafluoroethane/1,1,1,2-tetrafluoroethane=23:25:52 (weight ratio) were placed, and the operation of the rotary compressor was continued for 500 hours at the compressor shell top temperature of 130° C. (discharge pressure: 31 kgf/cm², inlet pressure: 2 kgf/cm²). After the completion of the test, the wear amount of the vane tip and acid value of the ester compound were measured.

The results are shown in Table 11. As obvious from Table 11, working fluid compositions for a refrigerating machine using an ester compound having a kinematic viscosity at 40° C. of not lower than 40 mm²/s or a branched carboxylic acid ratio of not lower than 80 mol % are better than those using an ester compound having a kinematic viscosity at 40° C. of lower than 40 mm²/s or a branched carboxylic acid ratio of lower than 80 mol %, with showing a lower wear amount and a lower acid value. The working fluid compositions for a refrigerating machine, which use, among the ester compounds having a kinematic viscosity at 40° C. of not lower than 40 mm²/s and a branched carboxylic acid ratio of not lower than 80 mol %, a carboxylate mixture formed between pentaerythritol and 2-ethylhexanoic acid/3,5,5-trimethylhexanoic acid or a carboxylate mixture formed between pentaerythritol and 2-ethylpentanoic acid/2-methylhexanoic acid/2-ethylhexanoic acid/3,5,5-trimethylhexanoic acid, are excellent.

TABLE 11

| Ester compound | Viscosity of ester compound at 40° C. (mm²/s) | Branched ratio (%) | Wear amount (μm) | Acid value of ester compound after test (mgKOG/g) |
| --- | --- | --- | --- | --- |
| 13 | 61.8 | 100 | 19 | 0.55 |
| 14 | 70.2 | 100 | 14 | 0.49 |
| 28 | 60.4 | 100 | 18 | 0.64 |
| 19 | 68.3 | 100 | 15 | 0.60 |
| 6 | 52.1 | 100 | 25 | 0.98 |
| 16 | 30.7 | 100 | 30< | 3< |
| 17 | 31.5 | 100 | 30< | 3< |
| H | 68.8 | 76 | 18 | 1.51 |
| O | 56.7 | 79 | 28 | 3< |

TEST EXAMPLE 8

Next, with working fluid compositions for a refrigerating machine using the ester compound of the present invention, a compressor test was carried out using a commercially available rotary compressor for room air conditioners.

In a 1 kw rotary compressor (G515QB1X manufactured by Hitachi, Ltd.), 450 g of an ester compound of which water content had previously been adjusted to not higher than 20 ppm in advance and 160 to 180 g of a mixture of difluoromethane/pentafluoroethane/1,1,1,2-tetrafluoroethane=23:25:52 (weight ratio) were placed, and the operation of the rotary compressor was continued for 400 hours at the compressor shell top temperature of 130° C. (discharge pressure: 26 kgf/cm², inlet pressure: 5 kgf/cm²). After the completion of the test, acid value of the ester compound was measured. The results are shown in Table 12.

Figure 5:
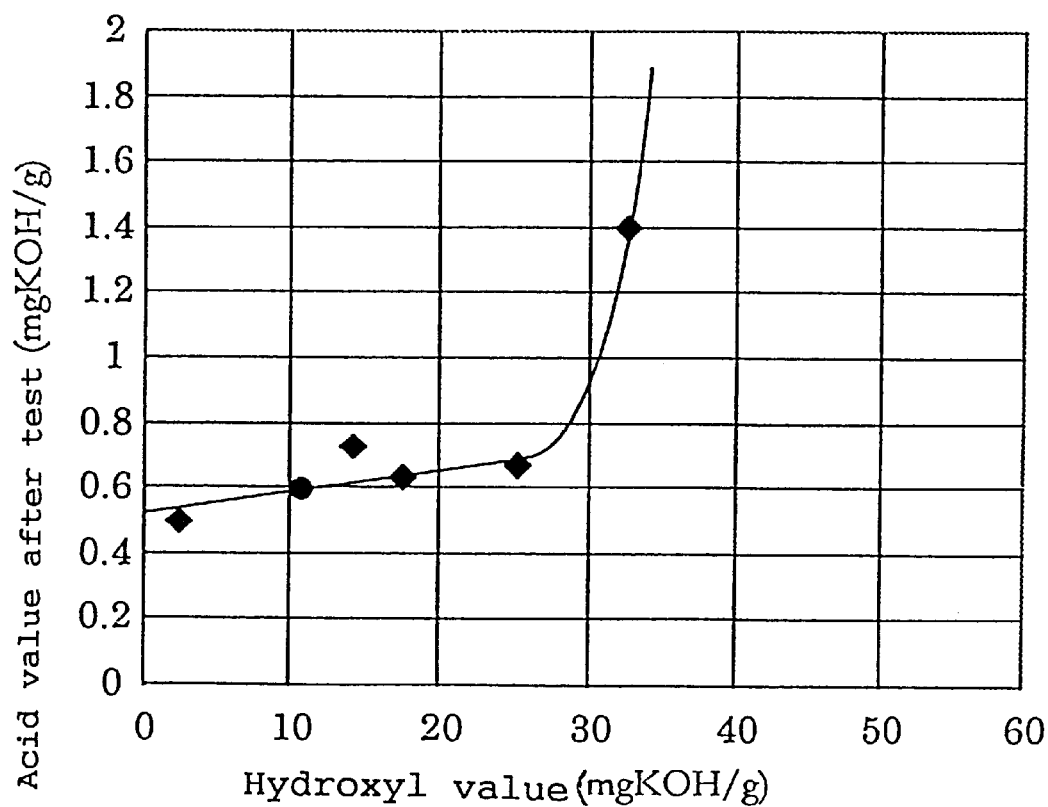
FIG. 5 is a graph which shows the relation between hydroxyl value/branched ratio and acid value after a compressor test of ester compounds. The horizontal axis is hydroxyl value of ester compounds, and the vertical axis is acid value measured after a compressor test of ester compounds. ♦ is the data of an ester compound having a branched ratio of 100 mol %, and ● is the data of an ester compound having a branched ratio of 90 mol %.
Figure 6:
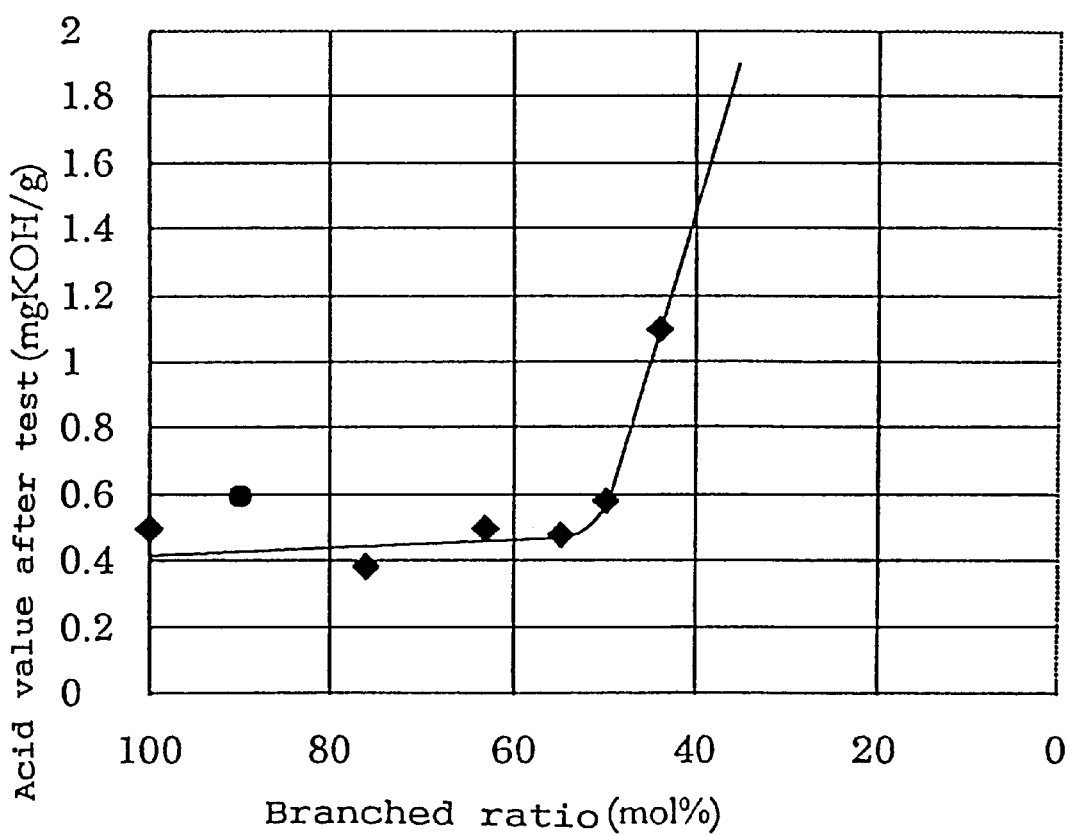
FIG. 6 is a graph which shows the relation between hydroxyl value/branched ratio and acid value after a compressor test of ester compounds. The horizontal axis is branched ratio of ester compounds, and the vertical axis is acid value after a compressor test of ester compounds. ♦ is the data of an ester compound having a hydroxyl value of not more than 10 mg KOH/g, and ● is the data of the ester compound "d."

Also, graphs showing the relation of hydroxyl value, branched ratio and acid value measured after the above test of the ester compounds are shown in FIGS. 5 and 6. Also, a diagram of the apparatus used in the present test example is shown in FIG. 1.

TABLE 12

| Ester compound | Viscosity of ester compound at 40° C. (mm²/s) | Hydroxyl Value of ester compound (mgKOH/g) | Branched ratio (%) | Acid value of ester compound after test with rotary-type compressor (mgKOH/g) | Acid value of ester compound after test with reciprocating compressor (mgKOH/g) |
| --- | --- | --- | --- | --- | --- |
| 14 | 70.2 | 2.4 | 100 | 0.50 | 0.10 > |
| 27 | 71.5 | 14.3 | 100 | 0.73 | 0.10 > |
| L | 72.1 | 17.6 | 100 | 0.63 | 0.10 > |
| a | 73.0 | 25.1 | 100 | 0.67 | 0.10 > |
| d | 67.0 | 11.5 | 90 | 0.60 | 0.10 > |
| H | 68.8 | 1.1 | 76 | 0.38 | 0.10 > |
| I | 55.3 | 1.5 | 63 | 0.50 | 0.10 > |
| o | 45.4 | 0.35 | 55 | 0.48 | 0.10 > |
| v | 53.1 | 2.2 | 50 | 0.58 | 0.10 > |
| b | 73.5 | 32.5 | 100 | 1.4 | 0.10 > |
| M | 30.4 | 3.2 | 44 | 1.1 | 0.10 > |

Table 12 and the graphs shown in FIGS. 5 and 6 show that ester compounds 14, 27, L, a, and d, each having a hydroxyl value of not higher than 30 mg KOH/g and a branched ratio of not lower than 90 mol %, have good thermal stability, with showing a smaller increase in acid value after the test. On the contrary, ester compounds having a hydroxyl value of higher than 30 mg KOH/g are found to have poor thermal stability, with showing high acid values, even though the branched ratio is 100 mol % (e.g., ester compound b of which hydroxyl value is 32.5 mg KOH/g).

The results with ester compounds 14, H, I, o, v, and M, which have a hydroxyl value of not higher than 10 mg KOH/g, indicate that those having a branched ratio of not lower than 50 mol % have good thermal stability, with showing a small increase in acid value after the test.

In a 150 w reciprocating compressor, 310 g of an ester compound of which water content had previously been adjusted to not higher than 20 ppm and about 30 g of 1,1,1,2-tetrafluoroethane were placed, and a 1000-hour continuous operation test was carried out under the conditions of a temperature at the compressor shell of 90° C., a discharge pressure of 24 kgf/cm$^2$, and an inlet pressure of 0.7 kgf/cm$^2$. The acid value of the ester compound after the completion of the test was measured.

The results are shown in Table 12. From Table 12, it is known that in a reciprocating compressor where the temperature and pressure are lower than in a rotary compressor, the increase in acid value after the test is small regardless of the hydroxyl value or branched ratio of the ester compound and that ester compounds are not required to have high thermal stability as required for the present inventive product.

INDUSTRIAL APPLICABILITY

The present invention provides an ester compound having markedly good thermal stability in the presence of a metal, a lubricating oil composition and a working fluid composition for a refrigerating machine containing the ester compound as the main component. The present invention further provides a method for preventing thermal degradation of a lubricating oil when the ester compound is used as a base oil in the lubricating oil in the presence of a metal, especially in the presence of a refrigerant containing difluoromethane. Also, by blending as a base oil the ester compound of the present invention with a lubricating oil for rotary compressors or scroll compressors for refrigerating machines, high thermal stability in the presence of a metal, especially in the presence of a metal and a refrigerant containing difluoromethane, can be obtained. Furthermore, by blending as a base oil the ester compound of the present invention with a lubricating oil for compressors of room air conditioners or packaged air conditioners, high thermal stability in the presence of a metal, especially in the presence of a metal and a refrigerant containing difluoromethane, can be obtained.

What is claimed is:

1. A method for lubricating a metal in a compressor selected from the group consisting of a compressor for room air conditioners and a compressor for packaged air conditioners, comprising:
    contacting said metal in said compressor with a thermally stable lubricant composition comprising:
        a lubricating based oil consisting essentially of a fully esterified ester compound formed from a tetrahydric hindered alcohol having 5 to 15 carbon atoms, or mixtures thereof; and a saturated aliphatic monocarboxylic acid having 3 to 20 carbon atoms or mixtures thereof; wherein the ratio of a branched carboxylic acid to the entire carboxylic acids is between 80 and 99 mol %; wherein the hydroxyl value of the ester compound is not more than 10 mg KOH/g wherein the acid value of said ester compound is not more than 1.0 mg KOH/g, provided that the acid value is measured after carrying out the steps comprising placing in a 1 kW rotary compressor (G515QB1X, manufactured by Hitachi, Ltd.) 450 g of an ester compound containing not more than 20 ppm of water and a difluoromethane/pentafluoroethane/1,1,1,2-tetrafluoroethane mixture at a weight ratio of 23:25:52, adjusting a shell top temperature of the compressor to 130° C., a discharge pressure to 26 kgf/cm$^2$ and a suction pressure to 5 kgf/cm$^2$, and continuously running the compressor for 400 hours; and
    wherein the ester is in contact with a refrigerant consisting of a difluoromethane/pentafluoroethane/1,1,1,2-tetrafluoroethane mixture at a weight ratio of 23:25:52.

2. The method according to claim 1, wherein the kinematic viscosity at 40° C. of the ester compound is 2 to 1000 mm$^2$/s.

3. The method according to claim 1, wherein the hindered alcohol is pentaerythritol.

4. The method according to claim 1, wherein said saturated aliphatic monocarboxylic acid is selected from the group consisting of 2-ethylpentanoic acid, 2-methylhexanoic acid, 2-ethylhexanoic acid and 3,5,5-trimethylhexanoic acid.

5. A method for lubricating a metal in a compressor selected from the group consisting of a compressor for room air conditioners and a compressor for packaged air conditioners, comprising:
    contacting said metal in said compressor with a thermally stable lubricant composition comprising:
        a lubricant based oil consisting essentially of a fully esterified ester compound formed from a tetrahydric hindered alcohol having 5 to 15 carbon atoms, or mixtures thereof; and a saturated aliphatic monocarboxylic acid having 3 to 20 carbon atoms or mixtures thereof; wherein the ratio of a branched carboxylic acid to the entire carboxylic acids is between 80 and 98 mol %; wherein the hydroxyl value of the ester compound is not more than 10 mg KOH/g; wherein the acid value of said ester compound is not more than 1.0 mg KOH/g, provided that the acid value is measured after carrying out the steps comprising placing in a 1 kW rotary compressor (G515QB1X, manufactured by Hitachi, Ltd.) 450 g of an ester compound containing not more than 20 ppm of water and a difluoromethane/pentafluoroethane/1,1,1,2-tetrafluoroethane mixture at a weight ratio of 23:25:52, adjusting a shell top temperature of the compressor to 130° C., a discharge pressure to 26 kgf/cm$^2$ and a suction pressure to 5 kgf/cm$^2$, and continuously running the compressor for 400 hours; and
    wherein the ester is in contact with a refrigerant consisting of difluoromethane/pentafluoroethane/1,1,1,2-tetrafluoroethane at a weight ratio of 23:25:52.

6. The method according to claim 5, wherein the acid value as measured by the test defined in claim 5 is not more than 0.7 mg KOH/g.

* * * * *